United States Patent
Andersen et al.

(10) Patent No.: US 9,249,189 B2
(45) Date of Patent: Feb. 2, 2016

(54) ALPHA-FETOPROTEIN "RING AND TAIL" PEPTIDES

(75) Inventors: Thomas T. Andersen, Albany, NY (US); Herbert I. Jacobson, Albany, NY (US); James A. Bennett, Delmar, NY (US); Leroy Joseph, Albany, NY (US); Alberto Bryan, Philadelphia, PA (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 0 days.

(21) Appl. No.: 13/522,882

(22) PCT Filed: Jan. 18, 2011

(86) PCT No.: PCT/US2011/021560
§ 371 (c)(1),
(2), (4) Date: Oct. 29, 2012

(87) PCT Pub. No.: WO2011/088462
PCT Pub. Date: Jul. 21, 2011

(65) Prior Publication Data
US 2013/0059794 A1 Mar. 7, 2013

Related U.S. Application Data

(60) Provisional application No. 61/295,897, filed on Jan. 18, 2010.

(51) Int. Cl.
*C07K 7/52* (2006.01)
*C07K 7/64* (2006.01)
*A61K 38/00* (2006.01)
*A61K 38/12* (2006.01)

(52) U.S. Cl.
CPC ... *C07K 7/52* (2013.01); *C07K 7/64* (2013.01); *A61K 38/00* (2013.01)

(58) Field of Classification Search
CPC ............. C07K 5/12; C07K 7/64; C07K 11/02
See application file for complete search history.

(56) References Cited

U.S. PATENT DOCUMENTS

| | | | |
|---|---|---|---|
| 5,674,842 A | 10/1997 | Mizejewski | |
| 5,707,963 A | 1/1998 | Mizejewski | |
| 6,121,236 A | 9/2000 | Ben-Sasson | |
| 6,306,832 B1 | 10/2001 | Pietras | |
| 6,348,567 B1 | 2/2002 | Krystal et al. | |
| 6,818,741 B2 * | 11/2004 | Andersen et al. | 530/328 |
| 7,122,522 B2 * | 10/2006 | Andersen et al. | 514/19.4 |
| 7,132,400 B2 * | 11/2006 | Andersen et al. | 514/10.2 |
| 7,220,402 B1 * | 5/2007 | Andersen et al. | 424/9.341 |
| 7,598,342 B2 * | 10/2009 | Andersen et al. | 530/300 |
| 7,943,577 B2 * | 5/2011 | Andersen et al. | 514/19.9 |
| 2005/0271587 A1 | 12/2005 | Andersen et al. | |
| 2008/0039403 A1 * | 2/2008 | Andersen et al. | 514/16 |
| 2009/0203624 A1 | 8/2009 | Andersen et al. | |

OTHER PUBLICATIONS

Parikh et al. (Clin. Cancer Res. 2005 11: 8512-8520).*
Joseph, L. C. (Ph.D. Thesis Albany Medical College, May 26, 2009).*
Fexby and Bülow (Trends in Biotech. Oct. 2004 22(10): 511-516).*
Shibata et al. (Biooragnic & Medicinal Chem. Lett. 2003 13:2583-2586).*
Penn State U. (Administration by Oral Gavage, http://www.research.psu.edu/arp/experimental-guidelines/administration-by-oral-gavage, Dec. 31, 2013).*
International Search Report for PCT/US2011/021560 dated Apr. 23, 2012.
Leroy C. Joseph, et al.; "Antiestrogenic and anticancer activities of peptides derived from the active site of alpha-fetoprotein," Journal of Peptide Science, vol. 15, No. 4, Apr. 1, 2009, pp. 319-325.
Karl N. Kirschner, et al.: "Computational Design and Experimental Discovery of an Antiestrogenic Peptide Derived from [alpha]-Fetoprotein," Journal of the American Chemical Society, vol. 129, No. 19, May 1, 2007, pp. 6263-6268.
Mesfin F B et al.: "Alpha-Fetoprotein-Derived Antiestrotrophic Octapeptide," Biochimica et Biophysica Acta. Molecular Basis of Disease, Amsterdam, NL, Jan. 1, 2000, pp. 33-43.
Jacobson et al , "Inhibition of Estrogen-dependent Breast Cancer Growth by a Reaction Product of α-Fetoprotein and Estradiol", *Cancer Research* vol. 50, 415-420, Jan. 15, 1990.
Bennett et al., "α-Fetoprotein Derived from a Human Hepatoma Prevents Growth of Estrogen-dependent Human Breast Cancer Xenografts", *Clinical Cancer Research*, vol. 4, 287-2884, Nov. 1998.
Mesfin et al., "Development of a synthetic cyclized peptide derived from α-fetoprotein that prevents the growth of human breast cancer", *J. Peptide Res.*, 2001, vol. 58, 246-256.
Defreest et al., "Synthetic peptide derived from α-fetoprotein inhibits growth of human breast cancer: investigation of the pharmacophore and synthesis optimization", *J. Peptide Res.*, 2004, vol. 63, 409-419.
Bennett et al., "A peptide derived from alpha-fetoprotein prevents the growth of estrogen-dependent human breast cancers sensitive and resistant to tamoxifen", *PNAS*, 2002; vol. 99, 2211-2215.
Eisele et al., "Studies on a growth-inhibitory peptide derived from alpha-fetoprotein and some analogs", *J. Peptide Res.*, 2001, vol. 57, 29-38.
Eisele et al., "Studies on analogs of a peptide derived from alpha-fetoprotein having antigrowth properties", *J. Peptide Res.*, 2001, vol. 57, 539-546.
Aggarwal et al., "Synthesis and Screening of a Random Dimeric Peptide Library Using the One-Bead-One Dimer Combinatorial Approach", *Bioconjugate Chem.*, 2006, vol. 17, 335-340.
Aggarwal et al., "A Dimeric Peptide that Binds Selectively to Prostate-Specific Membrane Antigen and Inhibits its Enzymatic Activity", *Cancer Res 2006*, vol. 66: (18): 9171-9177 Sep. 15, 2006.

(Continued)

*Primary Examiner* — Peter J Reddig
(74) *Attorney, Agent, or Firm* — Heslin Rothenberg Farley and Mesiti, PC; Kathy Smith Dias

(57) ABSTRACT

The invention relates to compounds that are analogs of a cyclic peptide, cyclo[EKTOVNOGN] (SEQ ID NO: 13), AFPep, that has anti-estrotrophic activity. The analogs of the invention include peptides and peptidomimetics that inhibit estrogen receptor-dependent cell proliferation. The compounds of the invention are useful for treating cell proliferative disorders or physiological conditions characterized by undesirable or unwanted estrogen induced cell proliferation, including breast cancer.

15 Claims, 12 Drawing Sheets

(56) References Cited

OTHER PUBLICATIONS

O'Leary et al., "Design of Potent Peptide Mimetics of Brain-derived Neurotrophic Factor", *The Journal of Biological Chemistry*, vol. 278, No. 28, Jul. 11, 2003, 25738-25744.

Kirschner et al., "Computational Design and Experimental Discovery of an Anti-estrogenic Peptide Derived from Alpha-Fetoprotein", *J. Am. Chem. Soc.*, 2007, vol. 129(19), 6263-6268.

Parikh et al., "Prevention of N-Methyl-N-Nitrosourea-Induced Breast Cancer by α-Fetoprotein (AFP)—Derived Peptide, a Peptide Derived from the Active Site of AFP", *Clin Cancer Res*, 2005; 11(23) Dec. 1, 2005; 8512-8520.

Mizejewski et al., "α-Fetoprotein growth inhibitory peptides: Potential leads for cancer therapeutics", *Mol Cancer Ther.*, 2003;2: 1243-1255.

Mesfin et al., "Alpha-fetoprotein-derived antiestrotrophic octapeptide", *Biochimica et Biophysica Acta* 1501 (2000) 33-43.

Joseph, L.C., et al. "Antiestrogenic and anticancer activities of peptides derived from the active site of alpha-fetoprotein", *Journal of PeptideScience*, 15, pp. 319-312 (2009).

Joseph , L.C., Second Generation Analogs of the anticancer peptide AFPep: Enhancement of Efficacy and Dose Range, *ProQuest, UMI Dissertations Publishing*, 3364558 (2009).

Fexby, S. et al., "Hydrophobic Peptide Tags as Tools in Bioseparation", *Trends in Biotechnology*, 22(10) 2004.

Shibata, K., et al., "Improvement of Biological Activity and Proteolytic Stability of Peptides by Coupling with a Cyclic Peptide", *Bioorganic & Medicinal Chemistry Letters*, 13, pp. 2583-2586 (2003).

Penn State University (Administration by Oral Gavage, http://www.research.psu.edu/arp/experimental-guidelines/administration-by-oral-gavage, Dec. 30, 2013.

* cited by examiner

SEQUENCE LISTING

<160> NUMBER OF SEQ ID NOS: 30

<210> SEQ ID NO 1
<211> LENGTH: 8

```
<212> TYPE: PRT
<213> ORGANISM: Artificial Sequence
<220> FEATURE:
<223> OTHER INFORMATION: Synthetic peptide

<400> SEQUENCE: 1

Glu Met Thr Pro Val Asn Pro Gly
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Thr Pro Val Asn
1

<210> SEQ ID NO 3
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyproline

<400> SEQUENCE: 3

Thr Xaa Val Asn
1

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Thr Pro Val Asn Pro
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyproline

<400> SEQUENCE: 5

Thr Xaa Val Asn Pro
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
```

```
<222> LOCATION: (5)..(5)
<223> OTHER INFORMATION: X is hydroxyproline

<400> SEQUENCE: 6

Thr Pro Val Asn Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyproline
<220> FEATURE:
<221> NAME/KEY: MOD_RES
<222> LOCATION: (5)..(5)
<223> OTHER INFORMATION: X is hydroxyproline

<400> SEQUENCE: 7

Thr Xaa Val Asn Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Pro Val Asn Pro Gly
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is hydroxyproline
<220> FEATURE:
<221> NAME/KEY: MOD_RES
<222> LOCATION: (4)..(4)
<223> OTHER INFORMATION: X is hydroxyproline

<400> SEQUENCE: 9

Xaa Val Asn Xaa Gly
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: X is hydroxyproline

<400> SEQUENCE: 10

Lys Thr Xaa Val Asn
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: X is hydroxyproline
<220> FEATURE:
<221> NAME/KEY: MOD_RES
<222> LOCATION: (6)..(6)
<223> OTHER INFORMATION: X is hydroxyproline

<400> SEQUENCE: 11

Lys Thr Xaa Val Asn Xaa
1               5

<210> SEQ ID NO 12
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: X is hydroxyproline
<220> FEATURE:
<221> NAME/KEY: MOD_RES
<222> LOCATION: (4)..(4)
<223> OTHER INFORMATION: X is hydroxyproline

<400> SEQUENCE: 12

Xaa Val Asn Xaa
1

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: X is hydroxyproline
<220> FEATURE:
<221> NAME/KEY: MOD_RES
<222> LOCATION: (7)..(7)
<223> OTHER INFORMATION: X is hydroxyproline

<400> SEQUENCE: 13

Glu Lys Thr Xaa Val Asn Xaa Gly Asn
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: X is hydroxyproline
<220> FEATURE:
<221> NAME/KEY: MOD_RES
<222> LOCATION: (6)..(6)
<223> OTHER INFORMATION: X is hydroxyproline
```

```
<400> SEQUENCE: 14

Lys Thr Xaa Val Asn Xaa Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Lys Thr Pro Val Asn Pro Gly
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic peptide

<400> SEQUENCE: 16

Thr Pro Val Asn Asn
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyproline

<400> SEQUENCE: 17

Thr Xaa Val Asn Asn
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic peptide

<400> SEQUENCE: 18

Thr Pro Val Asn Pro Asn
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyporline

<400> SEQUENCE: 19

Thr Xaa Val Asn Pro Asn
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (5)..(5)
<223> OTHER INFORMATION: X is hydroxyproline

<400> SEQUENCE: 20

Thr Pro Val Asn Xaa Asn
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: X is hydroxyproline
<220> FEATURE:
<221> NAME/KEY: MOD_RES
<222> LOCATION: (5)..(5)
<223> OTHER INFORMATION: X is hydroxyproline

<400> SEQUENCE: 21

Thr Xaa Val Asn Xaa Asn
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide

<400> SEQUENCE: 22

Pro Val Asn Pro Gly Asn
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: X is hydroxyproline
<220> FEATURE:
<221> NAME/KEY: misc_feature
<222> LOCATION: (4)..(4)
<223> OTHER INFORMATION: X is hydroxyproline

<400> SEQUENCE: 23

Xaa Val Asn Xaa Gly Asn
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MOD_RES
<222> LOCATION: (3)..(3)
<223> OTHER INFORMATION: X is hydroxyproline

<400> SEQUENCE: 24

Lys Thr Xaa Val Asn Asn
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: X is hydroxyproline
<220> FEATURE:
<221> NAME/KEY: MOD_RES
<222> LOCATION: (6)..(6)
<223> OTHER INFORMATION: X is hydroxyproline

<400> SEQUENCE: 25

Lys Thr Xaa Val Asn Xaa Asn
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: X is hydroxyproline
<220> FEATURE:
<221> NAME/KEY: MOD_RES
<222> LOCATION: (6)..(6)
<223> OTHER INFORMATION: X is hydroxyproline

<400> SEQUENCE: 26

Lys Thr Xaa Val Asn Xaa Gly Asn
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Lys Thr Pro Val Asn Pro Gly Asn
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
```

```
<223> OTHER INFORMATION: Xaa can be any naturally occurring amino acid

<400> SEQUENCE: 28

Thr Xaa Val Asn Xaa Gly Asn Glu Lys
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic peptide

<400> SEQUENCE: 29

Pro Gly Val Gly Gln
1               5

<210> SEQ ID NO 30
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 30

Glu Lys Thr Xaa Val Gly Xaa Gly Asn
1               5
```

ALPHA-FETOPROTEIN "RING AND TAIL" PEPTIDES

CROSS-REFERENCE TO RELATED APPLICATIONS

This application claims the priority of U.S. provisional application No. 61/295,897 filed Jan. 18, 2010, the contents of which are hereby incorporated by reference into the present application.

GOVERNMENT SUPPORT

The present application was made with support from the National Institutes of Health Grant Nos. 5R01 CA102540, R15 CA115524, 5R25 GM062460 and T34 GM008718 and Department of Defense Grant Nos. W81XWH-04-1-0486 and BC031067; National Science Foundation Grant Nos. CHE-0457275, CHE-0116435 and CHE-0521063. The U.S. Government has certain rights in this invention.

REFERENCE TO A SEQUENCE LISTING

The instant application contains a Sequence Listing, created on Jun. 3, 2014; the file, in ASCII format, is designated 0410018D_SequenceListing_ST25.txt and is 7.68 kilobytes in size. The file is hereby incorporated by reference in its entirety into the instant application.

FIELD OF THE INVENTION

The invention relates generally to peptides derived from alpha-fetoprotein and their use to treat and/or prevent cancer, including breast cancer, glioblastoma, malignant and benign tumors in the ovaries, uterus, prostate, and thyroid. In particular, the peptides of the invention are "ring and tail" cyclic peptides that exhibit anti-estrogenic activity.

BACKGROUND OF THE INVENTION

Alpha-fetoprotein (AFP) is an embryo specific serum alpha-globulin glycoprotein that is synthesized in the fetal yolk sac and circulates through the serum of pregnant women (G. I. Abelev 1971). In the last several decades, clinical researchers have investigated the potential anti-estrogen and anti-breast cancer activities of AFP (Jacobson et al. 1990). A number of studies have since shown its effectiveness as a therapeutic agent to treat estrogen-dependent breast cancer, as well as its ability to prevent pre-malignant foci from developing into breast cancer. Specifically, these studies indicate that alpha-fetoprotein (AFP) interferes with estrogen-dependent responses, including the growth-promoting effects of estrogen on breast cancer (Bennett et al. 1998). U.S. Pat. Nos. 5,674,842 and 5,707,963 relate to a 34-amino acid peptide derived from alpha-fetoprotein that was shown to exhibit anti-estrotrophic activity. Subsequently, an 8-amino acid stretch of AFP, EMTPVNPG, (SEQ ID NO. 1), referred to as peptide P472-2, was identified as possessing anti-estrotrophic activity (Mesfin et al. 2000). Furthermore, U.S. Pat. Nos. 6,818,741 and 7,122,522 describe peptides of eight to twenty amino acids, including a cyclic 9-mer (AFPep) that is useful in reducing estrogen-stimulated growth of cells. Finally, peptides as small as from 4-7 amino acids have been shown to retain anti-estrogenic activity (U.S. Pat. No. 7,598,342)

SUMMARY OF THE INVENTION

The present invention provides cyclic "ring and tail" peptides that are analogs of cyclo[EKTOVNOGN] (AFPep.) (SEQ ID NO: 13) The ring of the ring and tail analog comprises from five to nine amino acids including the sequence of the putative pharmacophore, XVNX' (SEQ ID NO: 12), where X and X' are independently proline or hydroxyproline. The cyclic peptides of the invention further comprise a tail portion comprising from 1-4 amino acids, where the tail portion is joined to the cyclic portion by an amide linkage to the side chain of the asparagine residue opposite the pharmacophore. In one embodiment, the cyclic ring and tail peptide of the invention has the structure shown in FIG. 1, where the "tail" is a single amino acid residue, for example phenylalanine, linked to the ring via the side chain amino group of asparagine.

Surprisingly, the peptides of the present invention retain, and in some instances, surpass the anti-estrotrophic activity of the 34-mer (P447), 8-mer (P472-2) and AFPep analog previously identified. The ring and tail peptides exhibited higher efficacy and a broader, more effective dose range.

In one aspect, therefore, the present invention relates to a cyclic peptide having a "ring and tail" structure, wherein the ring portion of said cyclic peptide contains from five to nine amino acids and comprises an amino acid sequence of $AA_1$-$AA_2$-N-$AA_3$, wherein $AA_1$ is proline, hydroxyproline or serine; $AA_2$ is valine, isoleucine, leucine or threonine; and $AA_3$ is proline or hydroxyproline; further, the tail portion of the ring and tail cyclic peptide is a linear peptide comprising from one to four amino acids. The ring and tail peptide of the invention has anti-estrotrophic activity.

In a related aspect, the invention relates to a cyclic peptide having a ring and tail structure, wherein the ring comprises an amino acid sequence selected from TPVN (SEQ ID NO: 2), TOVN (SEQ ID NO: 3), TPVNP (SEQ ID NO: 4), TOVNP (SEQ ID NO: 5), TPVNO (SEQ ID NO: 6), TOVNO (SEQ ID NO: 7), PVNPG (SEQ ID NO: 8), OVNOG (SEQ ID NO: 9), KTOVN (SEQ ID NO: 10), KTOVNO (SEQ ID NO: 11), KTOVNOG (SEQ ID NO: 14), KTPVNPG (SEQ ID NO: 15) and EKTOVNOGN (SEQ ID NO: 13).

In a related aspect, the invention relates to pharmaceutical compositions comprising the anti-estrotrophic ring and tail peptides of the invention.

In another aspect, the invention relates to pharmaceutical compositions comprising one or more ring and tail peptides of the invention and a pharmaceutically acceptable carrier. In one embodiment the pharmaceutical composition comprises a combination of a first ring and tail peptide having anti-estrogenic activity and a second ring and tail peptide having antagonist activity, wherein the combination of said first and second peptides has greater anti-estrogenic activity/broader dose range than said first peptide alone. The present invention, therefore, encompasses the use of the AFPep analogs of the invention for the treatment of diseases associated with estrogen-dependent growth of cells, including but not limited to breast cancer.

In a related aspect, the invention relates to a method of inhibiting the estrogen-dependent growth of cells, including breast tumor cells, using an anti-estrotrophic peptide of the invention. Accordingly, the peptide of the invention is useful in the treatment of diseases associated with estrogen-dependent growth, including breast cancer and uterine fibroids. Furthermore, the peptide of the invention may be used in conjunction with other breast cancer therapies, for example, to potentiate the efficacy of treatment with tamoxifen.

DETAILED DESCRIPTION OF THE INVENTION

All published patent applications, patents and other references cited herein are incorporated by reference in their entirety into the present disclosure.

The invention provides compounds including peptides and peptidomimetics that inhibit estrogen receptor dependent cell proliferation. The compounds of the invention are, therefore, useful for treating cell proliferative disorders or physiological conditions, including breast cancer, characterized by undesirable or unwanted estrogen induced cell proliferation.

In the description that follows, certain conventions will be followed as regards the usage of terminology.

Throughout the specification, the term "AFPep" is used to designate a cyclic peptide, cyclo[EKTOVNOGN] (SEQ ID NO: 13). For each analog described in the specification, the following convention is followed with respect to its amino acid composition: the amino acid sequence of the cyclic or "ring" portion of the cyclic peptide is indicated by brackets [ ], while the amino acid residues that comprise the tail are indicated following the brackets [ ]F or [ ]FI, with the amino acid attached to the ring listed first.

Amino acids that have hydrophobic side chains (alkane or aromatic) include alanine, phenylalanine, isoleucine, leucine, and valine. Any combination of amino acids that have a hydrophobic side chain can create a hydrophobic tail.

The term "peptide", as that term is know to those of skill in the art, refers to a molecule comprising two or more amino acids, generally fewer than fifty, where the alpha-carboxylic group of one is bound to the alpha-amino group of the other. The universal one letter code known to those skilled in the art is used herein for the identification of the twenty basic amino acids. Additionally, the one letter code, "O" is used herein to designate hydroxyproline, a hydroxylated derivative of proline.

Figure 1:
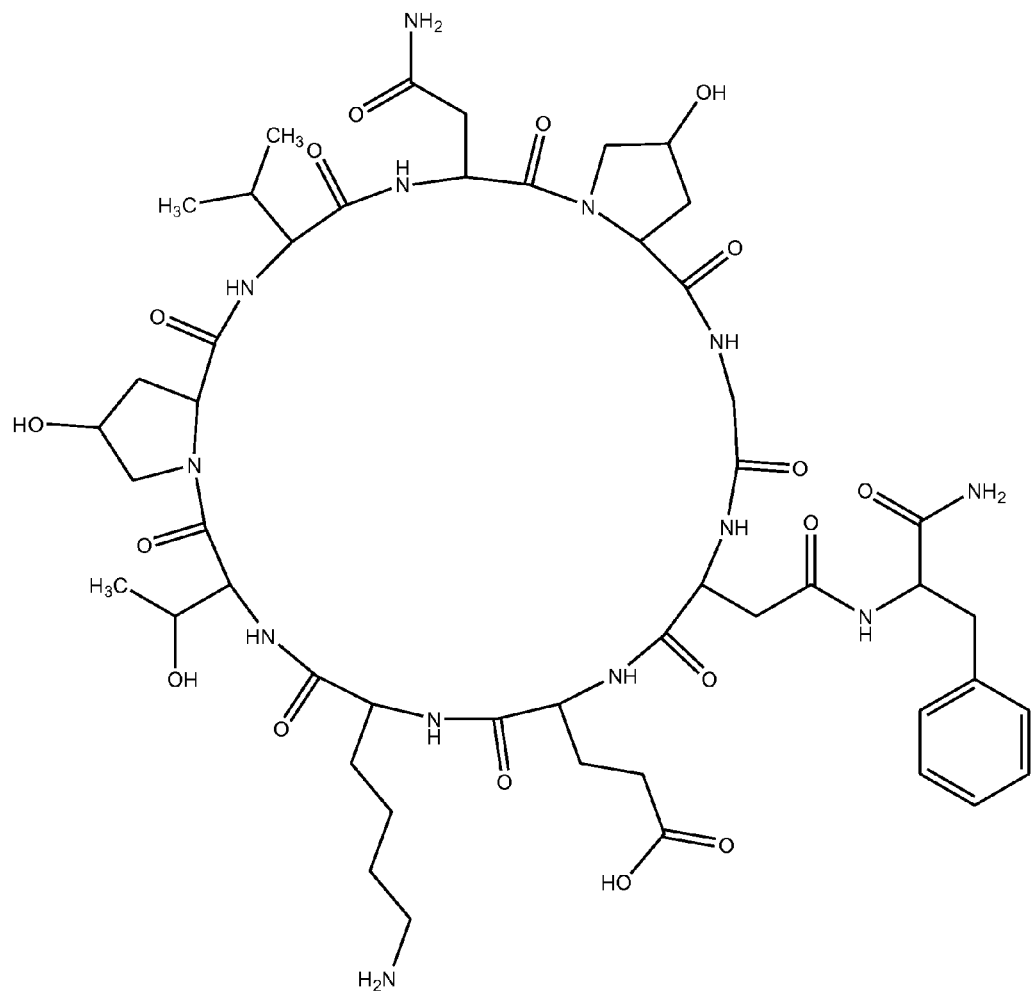
FIG. 1 depicts one embodiment of the "ring and tail" structure possessed by cyclic peptides of the invention. In this embodiment, the ring portion comprises nine amino acid residues, EKTOVNOGN, (SEQ ID NO: 13) and a tail portion comprising a single amino acid residue, phenylalanine, which is linked to the ring via the amine group of the side chain of the second asparagine residue in EKTOVNOGN (SEQ ID NO: 13).
Figure 2:
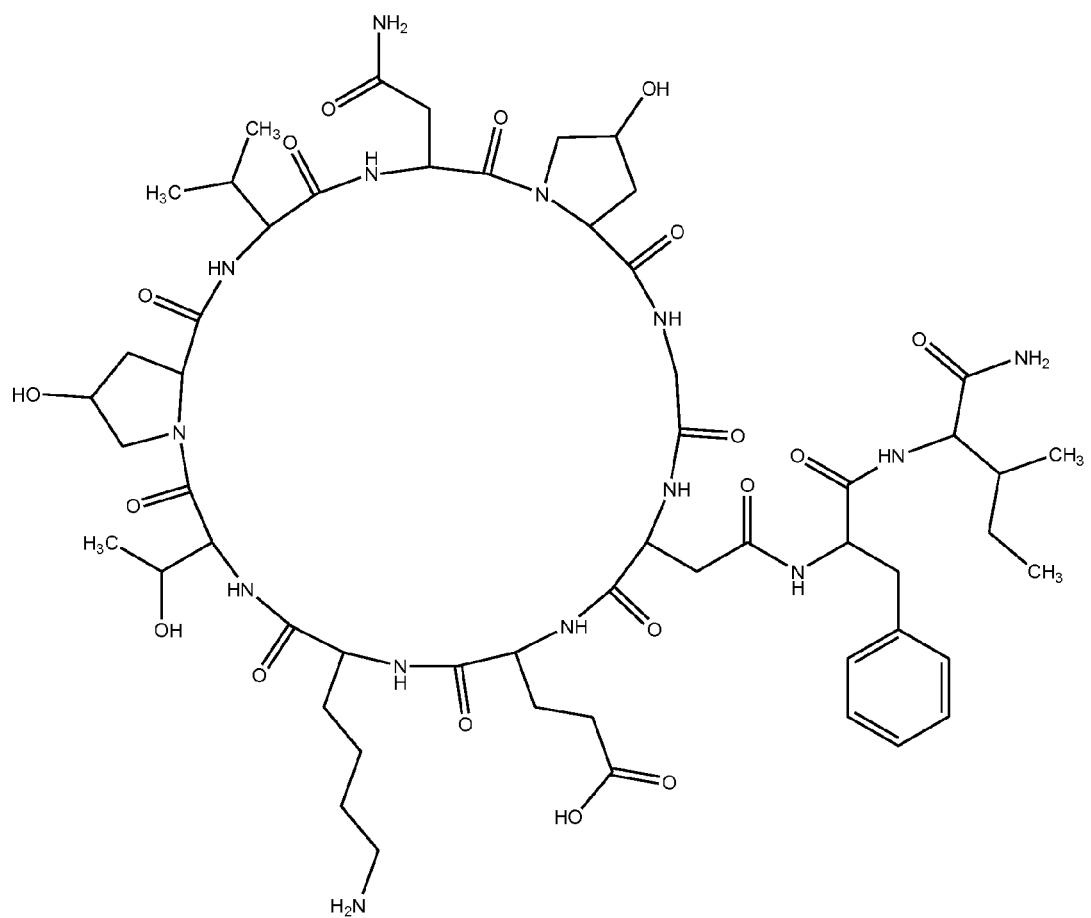
FIG. 2 depicts one embodiment of the "ring and tail" cyclic peptide of the invention. In this embodiment, the ring portion comprises nine amino acid residues, EKTOVNOGN (SEQ ID NO: 13), and a tail portion comprising two amino acid residues, phenylalanine and isoleucine, where the phenylalanine of the dipeptide tail is linked to the ring via the amine group of the side chain of the second asparagine residue in EKTOVNOGN (SEQ ID NO: 13).

In one embodiment, the present invention encompasses cyclic analogs of cyclo[EKTOVNOGN] (AFPep) (SEQ ID NO: 13). The analogs of the present invention comprise a "ring and tail" structure, for example as shown in FIG. 1. The "ring" comprises from five to nine amino acid residues including the putative pharmacophore, XVNX' (SEQ ID NO: 12), where X and X' are independently proline or hydroxyproline, and one asparagine residue outside of the putative pharmacophore. The "tail," which may be a linear peptide comprising from one to four amino acids, is linked to the ring via the side chain amino group of the non-pharmacophore asparagine residue.

In another embodiment, the invention encompasses a cyclic peptide, wherein the ring comprises the amino acid sequence, [EKTOVNOGN] (SEQ ID NO: 13). Other embodiments comprise amino acid sequences in which from one to four of the amino acid residues of the ring peptide are deleted or conservatively substituted.

In other embodiments, the invention encompasses a cyclic peptide having a ring and tail structure, wherein the ring comprises an amino acid sequence selected from TPVN (SEQ ID NO: 2), TOVN (SEQ ID NO: 3), TPVNP (SEQ ID NO: 4), TOVNP (SEQ ID NO: 5), TPVNO (SEQ ID NO: 6), TOVNO (SEQ ID NO: 7), PVNPG (SEQ ID NO: 8), OVNOG (SEQ ID NO: 9), KTOVN (SEQ ID NO: 10), KTOVNO (SEQ ID NO: 11), KTOVNOG (SEQ ID NO: 14), KTPVNPG (SEQ ID NO: 15) and EKTOVNOGN (SEQ ID NO: 13).

In still other embodiments, the invention encompasses a cyclic peptide having a ring and tail structure, wherein the ring comprises an amino acid sequence selected from TPVNN (SEQ ID NO: 16), TOVNN (SEQ ID NO: 17), TPVNPN (SEQ ID NO: 18), TOVNPN (SEQ ID NO: 19), TPVNON (SEQ ID NO: 20), TOVNON (SEQ ID NO: 21), PVNPGN (SEQ ID NO: 22), OVNOGN (SEQ ID NO: 23), KTOVNN (SEQ ID NO: 24), KTOVNON (SEQ ID NO: 25), KTOVNOGN (SEQ ID NO: 26), KTPVNPGN (SEQ ID NO: 27) and EKTOVNOGN (SEQ ID NO: 13).

In one embodiment, the invention relates to an antagonist of AFPep comprising the sequence cyclo[EKTOVNOGN] (SEQ ID NO: 13), where the first asparagines residue is substituted with a glycine residue. The antagonist is further modified by the addition of a tail comprising residues having hydrophilic side chains.

The terms "mimetic", "peptide mimetic" and "peptidomimetic" are used interchangeably, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

The terms "anti-estrotrophic activity" and "anti-estrotrogenic activity" refer to the ability of the peptides of the invention to inhibit or reduce the level of estrogen-dependent proliferation in an estrogen receptor-positive (ER+) cell population. Such activity can be measured in a variety of ways, including the immature mouse uterine growth assay as described by Bennett et al. 1998 and the human breast cancer xenograft assay as described by Bennett et al. 1998 and Jacobson et al. 1990.

The term "prevent" as that term is understood by the person of ordinary skill in the medical art (to which the present method claims are directed) is not an absolute term. In the medical art it is understood to refer to the prophylactic administration of a drug to substantially diminish the likelihood or seriousness of a condition. In the present context, the term refers to the ability of the peptides of the invention to lower incidence of palpable tumors, increase latency period and lower tumor multiplicity. The term is not intended to imply absolute protection from disease; rather it applies if there is a diminution in incidence and/or severity.

Peptides of the Invention

In one embodiment, the present invention relates to analogs of AFPep, that is, a cyclic peptide having a a ring portion containing from five to nine amino acids comprising an amino acid sequence contained within amino acids 489-496 of human alpha-fetoprotein (Genbank accession no. AAB58754), specifically TPVNP (SEQ ID NO: 4), and analogs thereof, for example, TOVNO (SEQ ID NO: 7).

Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention. (See for example, *Solid Phase Peptide Synthesis* by John Morrow Stewart and Martin et al. *Application of Almez-mediated Amidation Reactions to Solution Phase Peptide Synthesis*, Tetrahedron Letters Vol. 39, pages 1517-1520 1998.)

Short peptide sequences, or libraries of overlapping peptides which correspond to the selected regions described herein, can be readily synthesized and then screened in assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression. Methods for production of a peptide by recombinant DNA technology are well known to those of skill in the art.

cyclo[EKTOVNOGN] (AFPep) (SEQ ID NO: 13), a cyclic peptide derived from the active site of alpha-fetoprotein, has been shown to inhibit the growth of breast cancer. AFPep is comprised of 9 amino acids in head-to-tail peptide linkage. It was previously shown that linear analogs less than eight amino acids retained biological activity. Also, previous studies had suggested that aromaticity/hydrophobicity outside the ring (i.e. in the side chains) might enhance the biological activity of AFPep. Therefore, two hypotheses were tested: 1) Analogs with a smaller ring size than AFPep will have higher efficacy than AFPep and 2) an aromatic/hydrophobic amino acid residue(s) (i.e. a "tail") outside the ring will enhance dose-response properties. AFPep analogs were assembled on PAL-PEG-PS resin beginning with the C-terminus using N-terminally protected amino acids. Cyclic analogs were cyclized by formation of a peptide bond between the N-terminal residue and C-terminal residue in each amino acid sequence. Ring and tail peptide synthesis was carried out by adding one or more hydrophobic amino acids (Phe, Ile) to the optimal ring size to create a hydrophobic "tail," or by adding a hydrophilic amino acid (Lys, Glu, or Tyr) to create a hydrophilic "tail".

When cyclic peptides of various ring sizes were evaluated for antiestrogenic or anticancer activity, the 9-amino acid ring peptide (AFPep) was found to be the most effective. When a 'tail' was added, analogs with hydrophilic "tails" were found to have very weak biological activity, whereas analogs with hydrophobic "tails" significantly inhibited $E_2$-stimulated cancer cell growth in vivo and in vitro. cyclo[EKTOVNOGN] (SEQ ID NO: 13)FI was the most effective analog in inhibition of $E_2$-stimulated growth. It was significantly better than AFPep in inhibition of cancer cell growth and in its dose response profile. This new "ring and tail" design has produced a better anticancer agent than AFPep and this design could be adapted to evaluate receptor specificity.

A region of AFP was found to have anti-cancer properties. An 8-mer linear peptide was synthesized corresponding to this region and it retained the anti-cancer properties. However, its dose-response curve was biphasic portending a narrow dose range. In response to these observations a cyclic peptide (AFPep) was designed and synthesized and yielded a wider biphasic dose-response curve when evaluated in the uterine growth inhibition assay. Mass spectrometry revealed it had the correct molecular weight (peak=970 g/mol). However, in a study on AFPep, it was observed that a particular batch of AFPep exhibited an extended dose-response curve. On further examination of the data, the molecular weight of the cyclic peptide was found to be more than 160 g/mol higher than expected (peak=1136 g/mol). Another peak at 2105 g/mol, corresponds to a dimer of AFPep plus the putative linker group. Upon analysis of the synthesis method and analysis of the molecular weights (MW) of the reagents, it was suggested that the additional mass corresponded to a portion of the linker which attaches the peptide to the resin during synthesis. From these observations, it is logical to surmise that the putative linker group played a role in maintaining the activity of AFPep over a wider range of doses. Therefore, our intention is to develop cyclic analogs with a tail attachment. However, such analogs would be larger than 9-mer AFPep, and therefore more expensive to produce.

Therefore, before those analogs were developed, it was important to assess the smallest cyclic peptide that would be effective in inhibition of $E_2$-stimulated growth in vitro and in vivo. Recent results showed that analogs of AFPep less than 8 amino acid retained biological activity. It would be advantageous to invent active peptides with ring sizes smaller than 9 amino acids in order to accommodate the additional amino acid tails. DeFreest et al. had identified the pharmacophore region of AFPep, and suggested that it consists of only 4 amino acids, OVNO (SEQ ID NO: 12), and reasoned that the other amino acids were needed to lock AFPep in the right conformation. We surmised that cyclization of smaller analogs of AFPep would retain the pharmacophore, and therefore efficacy. Therefore, we evaluated the activity of cyclic peptides containing OVNO (SEQ ID NO: 12), but with as few additional amino acids as possible. An additional residue, Asp (OAll), is needed to close the ring of cyclic peptides, so we made cyclic peptides of 5 or more amino acids. Although 5 amino acids is a small ring size, synthesis of cyclic 5-amino acid rings has been achieved previously. Thus, we synthesized cyclic peptides of reducing ring size (from 9 amino acids to 5 amino acids ring size) to determine the smallest possible cyclic analog that would have antiestrogenic and anticancer activity equal or superior to AFPep.

During removal of the peptide from the resin (cleavage), there are three possible points at which cleavage can occur. When cleavage occurs at position 1 (normal cleavage), it results in the synthesis of AFPep with a MW=970 g/mol, which leads to the dose response curve shown in FIG. 4A. A cleavage of the resin at position 2 results in a product with MW=1136 g/mol and the dose response curve in FIG. 4B.

Figure 4:
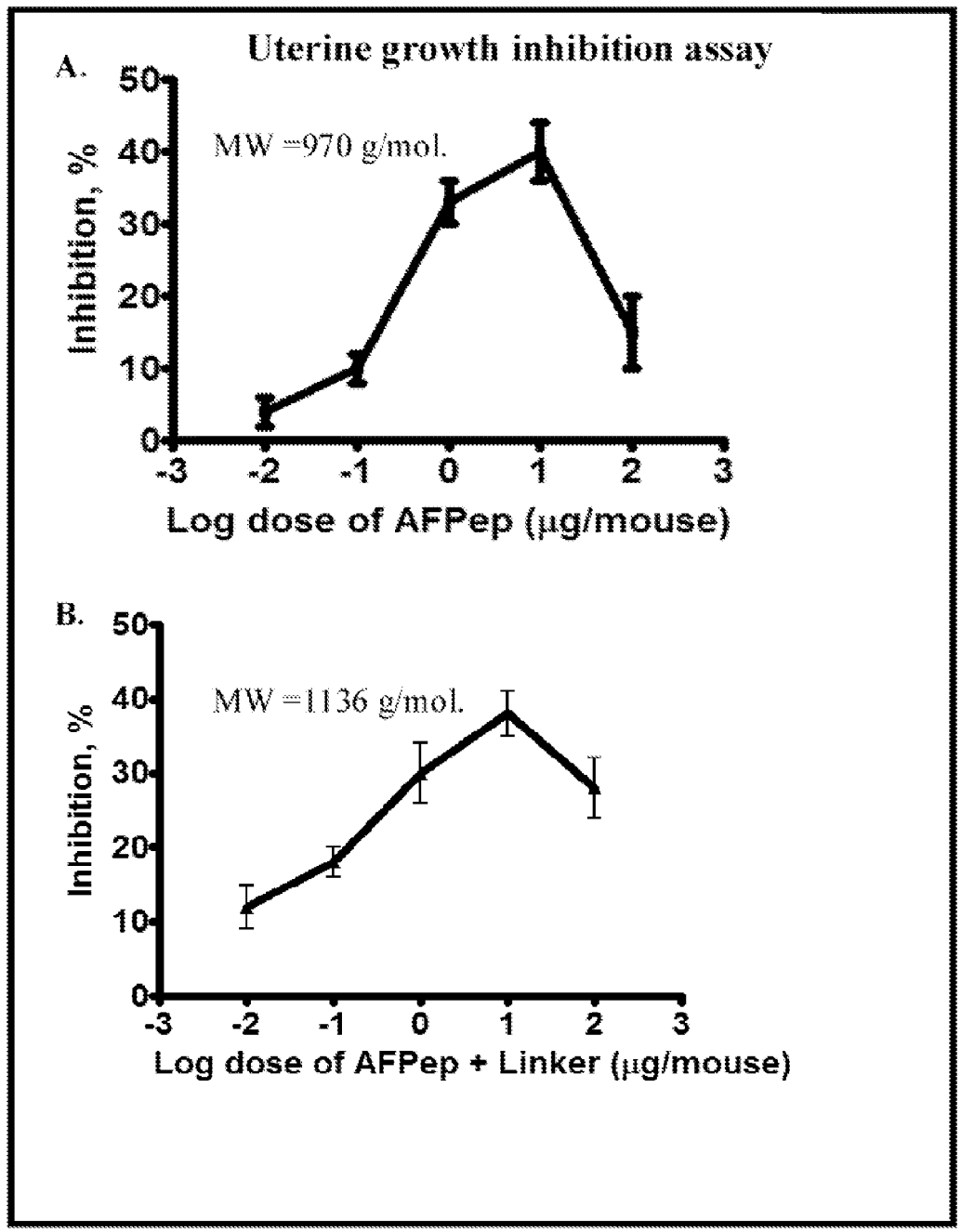
FIGS. 4(A) and (B) is a graph showing dose response curves for two AFPep preparations having different molecular weights.

It was hypothesized that the putative linker group was responsible for the wider dose range (FIG. 4B). The linker group attaching the peptide to the resin contains an aromatic ring with a number of hydrophobic (—$CH_3$) groups and some hydrophilic moieties (—OH). The putative linker group was attached to asparagine (N), distal to the pharmacophoric region of AFPep. Therefore, aromaticity/hydrophobicity, and the precise positioning of the 'tail' on the molecule constitute logical variables to manipulate in order to alter the shape of the dose response curve. We varied the hydrophobicity/hydrophilicity, aromatic/aliphatic nature, and size of the 'tail' of the optimal ring to explore the role of the putative linker group in structure and function. We kept the position of the tail constant, in doing so, avoided altering or blocking the pharmacophoric region of the molecule. Amino acids were attached onto N in AFPep, distal to the pharmacophore, to mimic the position of the putative linker group.

We used amino acids as opposed to chemical moieties to mimic the putative linker group because 1) amino acids are non-toxic 2) their side chains have different properties (changing from one amino acid to the next can readily change the structural feature of the 'tail') 3) they can be incorporated into the peptide sequence using the same synthetic technique for the synthesis of AFPep.

The strategy involved incorporating aspartate-allyl (Asp-OAl) directly onto the tail forming amino acids. The remainder to the sequence elongation was achieved by following standard Fmoc peptide synthesis described in material and methods. The ring is formed when the last amino acid that was added to the sequence forms a peptide bond with N, which allows the amino acids attached to the side chain of N to branch out as a tail. This led to the naming of this cyclic-tail peptide as 'ring and tail' peptide.

A number of studies have used this technique to synthesize peptides (called tailed cyclic peptide) to study cell adhesion. One of these studies gave a detail description of the design and synthesis of a five-member cyclic peptide ring bearing a six-carbon spacer arm fixed on the side chain of the peptide and ended with an anchoring cysteine at the C-terminal end of the arm. Delforge showed that endothelial cell adhesion was strongly promoted on bovine serum albumin modified with a RGD 'ring and tail' peptide. While our synthesis strategy is similar to the one used above, there are several differences. These studies used other moieties with amino acids to create the 'tail' of their peptides whereas we used only amino acids. Fmoc-Glu-OAl was used by Delforge et al. as the cyclizing amino acid whereas we used Fmoc-Asp-OAl. The major difference was that those studies focused on the utility of the 'ring and tail' peptides as adhesion molecules. In this study we are trying to improve the structure-activity relationship of AFPep. This may lead to a higher and a broader, more effective dose range.

The significance of this work is that if a 'ring and tail' peptide was to be developed that exhibits greater efficacy and a broader, more effective dose profile than AFPep in the inhibition of $E_2$-dependent growth of immature mouse uterus and T47D human ER+ breast cancer cells then this result could provide valuable tools for elucidating the target molecules of peptides which could aid in understanding the mode of action of AFP-derived peptides and could have obvious important clinical implications.

Design for Smaller Cyclic Analogs

Cyclic analogs of AFPep with reduced ring sizes (8 to 5 amino acids) were designed and synthesized (Table 1). The strategy was to maintain the putative pharmacophore of AFPep and the cyclizing amino acid residue, N, while eliminating amino acid residues that were not required for biological activity to obtain the optimal ring size. As shown in Table 1, 9-amino acid ring is AFPep; the 8-ring acid ring is missing residue E from AFPep; the 7-amino acids ring is missing residue E and G from AFPep; the 6-amino acid ring is missing residues E, K and G from AFPep; and the 5-amino acid ring is missing residues E, K, O, and G from AFPep.

TABLE 1

Design of cyclic analogs

| SEQ ID NO: | Peptide sequence | Ring size (number of amino acids) |
|---|---|---|
| 13 | cyclo [EKTOVNOGN] (AFPep) | 9 |
| 26 | cyclo [KTOVNOGN] | 8 |
| 25 | cyclo [KTOVNON] | 7 |
| 21 | cyclo [TOVNON] | 6 |
| 17 | cyclo [TOVNN] | 5 |

Antiestrogenic and Anticancer Activity of Cyclic Analogs

Four cyclic peptides of decreasing ring size (Table 1) were synthesized and were assessed for antiestrogenic activity using the immature mouse uterine assay. Negative control mice received saline alone. Positive control mice received $E_2$ alone. AFPep was used as a positive control peptide and cyclic Scr was used as a peptide control. Mice were injected intraperitoneally (i.p.) with each of these peptides at a dose of 1 μg/mouse. One hour later mice received 0.5 ug 17β-estradiol ($E_2$) i.p. Twenty-two hours later uteri were dissected, weighed, and normalized to body weight. The results are reported as mean±S.E (n=5) for four independent experiments.

Figure 5:
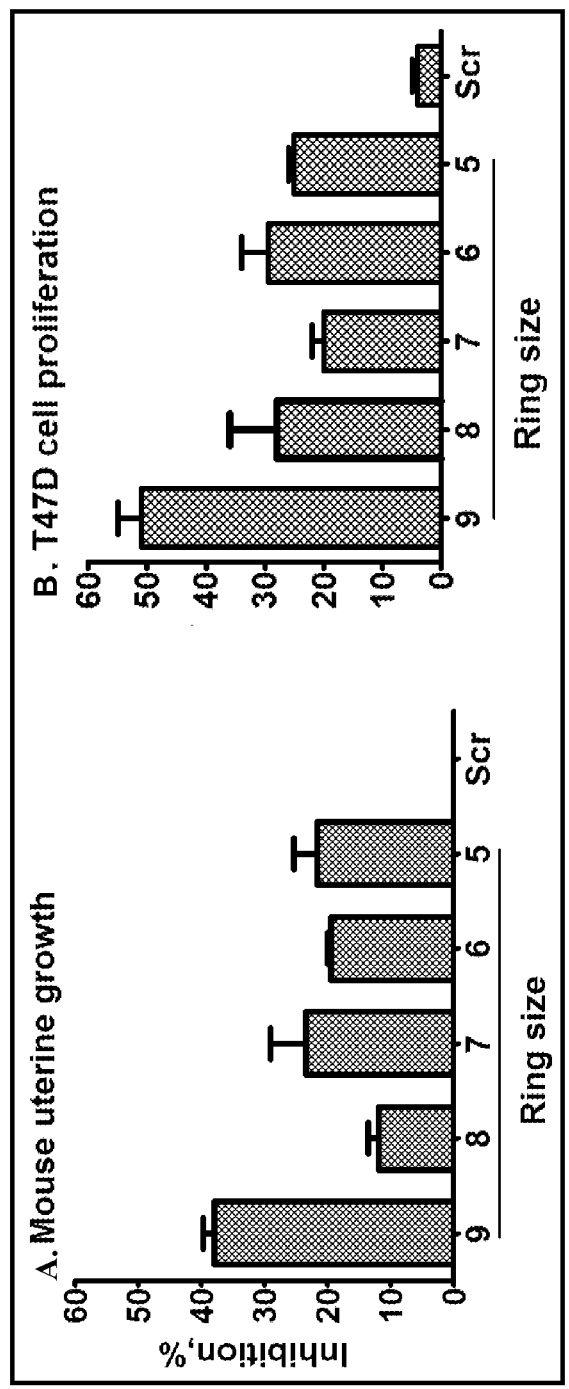
FIG. 5 is a graph showing the effect of ring size of AFPep analogs with respect to (A) inhibition of mouse uterine tissue growth and (B) inhibition of T47D human breast cancer cell proliferation

Anticancer activity of the cyclic peptides was also evaluated using the T47D cell proliferation assay. T47D cells were cultured on collagen-IV coated 24-well plates and treated with each of above peptides in the presence of $E_2$. Final peptide concentrations of each peptide were $10^{-6}$ M and final $E_2$ concentration was 1 nM. Values are reported as mean±SEM (n=6) of four independent experiments. AFPep was shown to be significantly different from the other analogs. However, the other ring sizes were not significantly different from each other. One-way ANOVA followed by Tukey's multiple comparison test. $p \le 0.05$ All of the cyclic analogs (except the negative control) exhibited antiestrogenic (FIG. 5A) and anticancer activity (FIG. 5B), with AFPep exhibiting significantly better inhibition of $E_2$-stimulated growth in vivo and in vitro than the other analogs with the analog with the 9-amino acid ring assessed to be the optimal ring size for effective inhibition of $E_2$-stimulated growth, the cyclic 9-mer was used as the core for subsequent building of ring and tail analogs.

Design for 'Ring and Tail' Analogs

In order to broaden the effective dose profile of cyclic AFPep peptide, nine analogs containing the 9-member ring and amino acid tails were designed and synthesized (Table 2).

The amino acid composition of the 'tail' was varied to assess the role of hydrophobicity or hydrophilicity, aromaticity or aliphaticity of the analogs. An analog will be considered hydrophobic when the tail residue(s) contain side chain(s) with an aromatic group or an aliphatic group or both (for example F, I, or FI). An analog will be considered hydrophilic if its side chain contains any polar or charged moieties (for example, Y, E, K, S, or YI, FS). The length of the 'tail' was varied by using 1 or 2 amino acids.

TABLE 2

Design of 'ring and tail' analogs

| 'Ring and Tail' Peptide | Properties of the 'Tail' | Amino acids side chain | Size of 'Tail' (No. of amino acids) |
| --- | --- | --- | --- |
| cyclo [EKTOVNOGN]* S | Hydrophilic | Alkyl/polar | 1 |
| cyclo [EKTOVNOGN]* Y | Hydrophilic | Aromatic/polar | 1 |
| cyclo [EKTOVNOGN]* K | Hydrophilic | Alkyl/polar | 1 |
| cyclo [EKTOVNGN]* E | Hydrophilic | Alkyl/polar | 1 |
| cyclo [EKTOVNOGN]* F | Hydrophobic | Aromatic | 1 |
| cyclo [EKTOVNOGN]* I | Hydrophobic | Alkyl | 1 |
| cyclo [EKTOVNOGN]* FS | Hydrophilic | Aromatic/alkyl/polar | 2 |
| cyclo [EKTOVNOGN]* YI | Hydrophilic | Aromatic/polar/alkyl | 2 |
| cyclo [EKTOVNOGN]* FI | Hydrophobic | Aromatic/alkyl | 2 |

*denotes amino acid sequence of SEQ ID NO: 13 in Table 2 and infra

Antiestrogenic and Anticancer Activity of Ring and Tail Analogs

We evaluated the effects that different tail residues would have on the antiestrogenic and anticancer activities of these ring and tail analogs. When these analogs were assessed for the ability to inhibit $E_2$-stimulated uterine growth and T47D human breast cancer cell growth, the hydrophobic analogs showed significant inhibition of growth, whereas the hydrophilic analogs exhibited insignificant inhibition (Table 3). Furthermore, cyclo[EKTOVNOGN] (SEQ ID NO: 13) was more effective at inhibiting $E_2$-stimulated growth than AFPep (Table 3).

A 'tail' was attached to a nine-amino acid ring and included 1 or 2 amino acids defined as hydrophilic or hydrophobic based on the nature of their side-chains. Tails comprising the following amino acid(s): serine (S), tyrosine (Y), lysine (L), glutamic acid (E), phenylalanine-serine (FS) and tyrosine-isoleucine (YI) represent hydrophilic tails and tails comprising the following amino acid(s), phenylalanine (F), isoleucine (I) and phenylalanine-isoleucine (FI) are hydrophobic tails. All peptides were administered at a dose of 1 μg/mouse intraperitoneally or 10 μg/mouse by oral gavage. Values are presented as mean±S.E. (n=5). In culture, T47D cells were treated with each peptide at a concentration of 1 μM. Values are presented as mean±S.E (n=6). Peptides with an inhibition of more than 25% significantly inhibited $E_2$-stimulated growth. *$p<0.05$ as compared to the group stimulated with $E_2$ alone. Wilcoxon Rank Sum Test.

Figure 6:
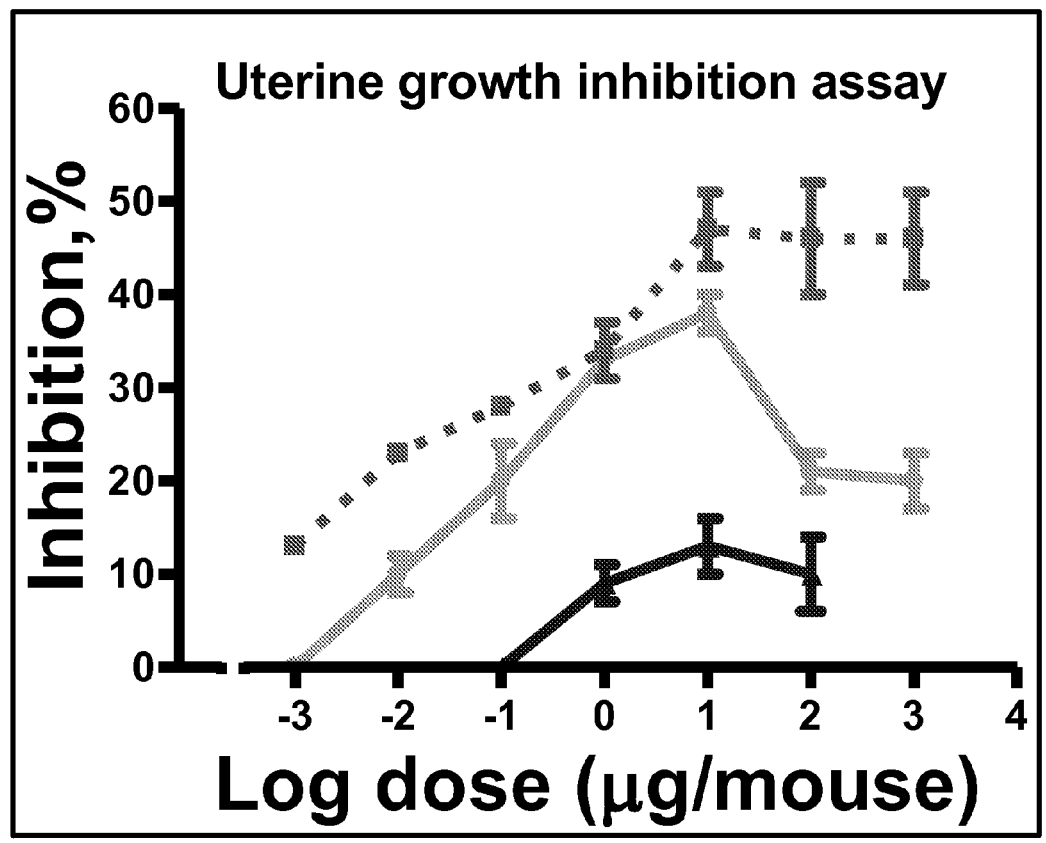
FIG. 6 is a graph showing the ability of ring and tail peptide analogs of AFPep (from top to bottom, cyclo[EKTOVNOGN] (SEQ ID NO: 13) FI, AFPep, and cyclo[EKTOVNOGN] (SEQ ID NO: 13) YI to inhibit $E_2$-induced uterine growth.

The results (shown in FIG. 6) indicated that adding a hydrophobic tail significantly improved the efficacy of the ring and tail peptide over AFPep. The next step was to determine if analogs maintained their effectiveness over a broader dose range that AFPep. Therefore, we assessed AFPep, cyclo [EKTOVNOGN] (SEQ ID NO: 13)YI, and cyclo[EKTOVNOGN] (SEQ ID NO: 13)FI for effectiveness as antiestrogenic agents over a number of doses. The results confirmed that the hydrophilic tail analogs, cyclo[EKTOVNOGN] (SEQ ID NO: 13)YI, had very little antiestrogenic activity. As has been shown in previous studies (26), AFPep significantly inhibited $E_2$-stimulated uterine growth to a dose of 10 μg and then loses its effectiveness at higher doses. The hydrophobic tail analog, cyclo[EKTOVNOGN] (SEQ ID NO: 13) FI, significantly inhibited $E_2$-stimulated growth in a dose-dependent manner and maintained its effectiveness at very high doses (FIG. 6).

Figure 7:
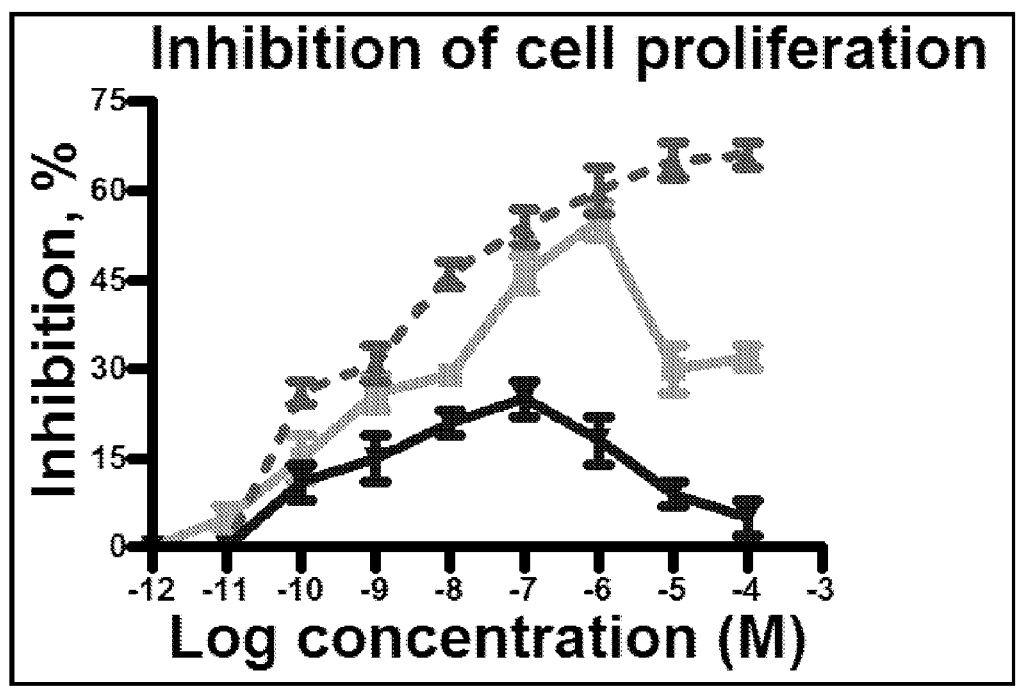
FIG. 7 is a graph showing the ability of ring and tail peptide analogs of AFPep (from top to bottom, cyclo[EKTOVNOGN] (SEQ ID NO: 13) FI, AFPep, and cyclo[EKTOVNOGN] (SEQ ID NO: 13) YI to inhibit T47D cell proliferation.

Together with cyclo[EKTOVNOGN] (SEQ ID NO: 13)YI, and AFPep, we assessed the anticancer activity of cyclo[EKTOVNOGN] (SEQ ID NO: 13)FI at different concentrations in vitro (FIG. 7). cyclo[EKTOVNOGN] FI inhibited $E_2$-stimulated T47D human breast cancer cell growth in a concentration-dependent manner, even at high concentrations. AFPep inhibited $E_2$-stimulated T47D cell growth up to a concentration of $10^{-6}$M and then loss its effectiveness at higher concentrations, which confirms results shown in section III. cyclo[EKTOVNOGN] (SEQ ID NO: 13)YI was ineffective against $E_2$-stimulated T47D human breast cancer cell growth.

To determine the effectiveness of cyclo[EKTOVNOGN] (SEQ ID NO: 13)FI as a potential cancer therapeutic agent in a clinically relevant model, we assessed the effect of cyclo [EKTOVNOGN] (SEQ ID NO: 13)FI on $E_2$-supplemented MCF-7 human breast cancer xenograft growth using different routes of administration. Briefly, a piece of MCF-7 human breast cancer measuring approximately 2 mm in average diameter was implanted under the kidney capsule of SCID mice. Mice were supplemented with $E_2$ pellets implanted subcutaneously, at the time of tumor implantation, for a steady state of $E_2$ at $10^{-9}$ M. Mice were treated with 10 μg subcutaneously (s.c.), 10 μg intraperitoneally (i.p.) or 100 μg orally (p.o.) cyclo[EKTOVNOGN] (SEQ ID NO: 13) FI was administered once daily from day 1 to day 20 of the experiment. Tumor size was measured as described in materials and methods. Data is presented as mean±S.E (n=5). After 20 days of treatment, the percentage change in tumor volume for each cyclo[EKTOVNOGN] (SEQ ID NO: 13)FI treated group was significantly different from the $E_2$ alone group. One-way ANOVA followed by Tukey's multiple comparison test. *$p<0.01$ vs. $E_2$.

Figure 8:
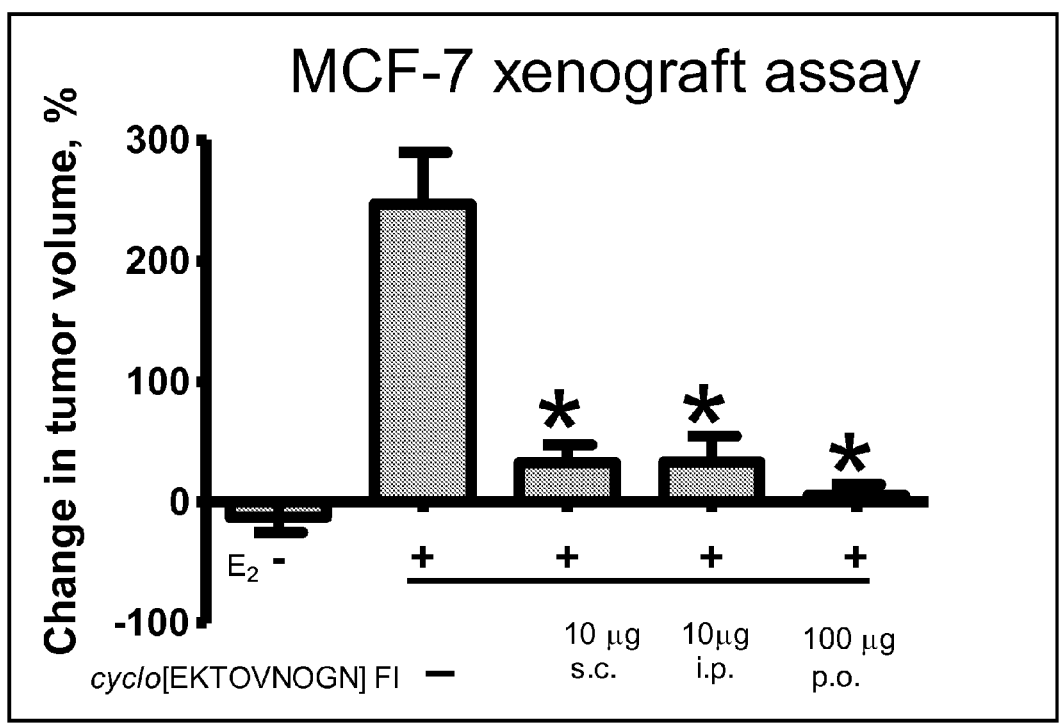
FIG. 8 shows the effect of different routes of administration of cyclo[EKTOVNOGN] (SEQ ID NO: 13)FI on its ability to inhibit growth of an MCF-7 xenograft in vivo.

FIG. 8 shows that cyclo[ETKOVNOGN] (SEQ ID NO: 13) FI significantly inhibited the growth of tumor xenografts, and there was no significant difference between the different routes of administration.

The anticancer activity of 'ring and tail' analogs was evaluated above in ER+ human breast cancer cells. The hydrophobic tail on AFPep enhanced its efficacy and dose response profile as antiestrogenic and anticancer agent. The next step was to determine whether cyclo[EKTOVNOGN] (SEQ ID NO: 13) FI would exhibit anticancer activity in ER− cells.

Estrogen independent (ER−)MDA MB231 cells were plated at 20,000 cells/well/ml in a collagen-IV coated 24-well plate. The next day, cells were treated with vehicle (0.1% ethanol), AFPep, cyclo[EKTOVNOGN] (SEQ ID NO: 13) YI, for 7 days. Each peptide was treated at $10^{-6}$ M. Cell proliferation was determined by MTT assay. Each value is the mean±S.E. (n=4) of three independent experiments.

Figure 9:
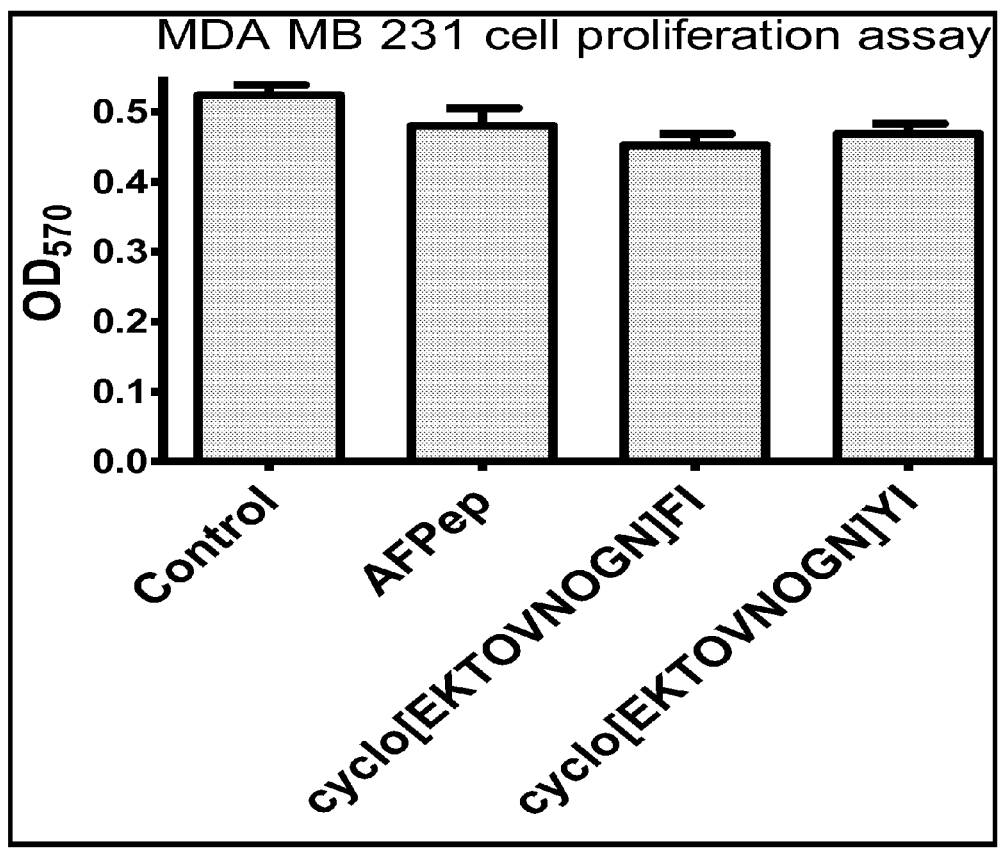
FIG. 9 shows the effect of ring and tail analogs on $E_2$-independent MDA-MB231 breast cancer cell growth.

FIG. 9 shows that cyclo[EKTOVNOGN] (SEQ ID NO: 13) FI had no effect on the growth of ER− MDA MB 231 cells in culture.

All peptides were administered at a dose of 1 μg/mouse intraperitoneally or 10 μg/mouse by oral gavage. Values are presented as mean±S.E (n=5). In culture, T47D cells were treated with each peptide at a concentration of 1 μM. Values are presented as mean±S.E (n=6). Peptides with an inhibition of more than 25% significantly inhibited $E_2$-stimulated growth. *p<0.05 as compared to the group stimulated with $E_2$ alone. Wilcoxon Rank Sum Test.

TABLE 3

Antiestrogenic and anticancer activity of 'ring and tail' peptides.

| Peptide sequence | Mouse uterine growth Inhibition ± S.E, % | | T47D cell proliferation |
|---|---|---|---|
| | Intra-peritoneal | Oral gavage | |
| cyclo[EKTOVNOGN]* | 38 ± 3* | 35 ± 4* | 51 ± 4* |
| cyclo[EKTOVNOGN]* S | 18 ± 2 | | 22 ± 6 |
| cyclo[EKTOVNOGN]* Y | 21 ± 2 | | 22 ± 3 |
| cyclo[EKTOVNOGN]* K | 17 ± 3 | | 18 ± 6 |
| cyclo[EKTOVNOGN]* E | 18 ± 3 | | 20 ± 2 |
| cyclo[EKTOVNOGN]* F | 37 ± 2* | | 46 ± 2* |
| cyclo[EKTOVNOGN]* I | 39 ± 2* | | 55 ± 6* |
| cyclo[EKTOVNOGN]* FS | 7 ± 3 | | |
| cyclo[EKTOVNOGN]* YI | 9 ± 5 | | 24 ± 3 |
| cyclo[EKTOVNOGN]* FI | 46 ± 4* | 35 ± 3* | 66 ± 2* |
| cyclo[EKTOVGOGN]* K | 7 ± 3 | | |

A strategy of for the synthesis of ring and tail peptides was developed in an effort to enhance the dose range of AFPep. In this strategy, amino acids forming the tail were first added onto the resin, and Fmoc-AspOAl was placed strategically in the peptide chain to form the ring. The number of amino acids preceding Fmoc-AspOAl, in the peptide chain, determined the length of the 'tail'. This gave the flexibility of developing peptides with 'tails' of any length for possible maximum interaction with its target molecule. However, it was not necessary to go beyond a tail length of 2 amino acids. The property of the amino acids side chains making up the 'tail' determined whether the 'ring and tail' peptides are considered hydrophobic or hydrophilic. This gave many options in the design of 'tails' for putative different efficacies/specificities. In order to assess the effects of the length and characteristics of the tail, we maintained the tail on the N residue distal to the pharmacophore of AFPep. Using amino acids in the 'tail' allowed us to maintain the integrity of the peptides (i.e. producing analogs without any known toxicity).

We have shown that the optimal 'ring and tail' analog (cyclo[EKTOVNOGN] (SEQ ID NO: 13) FI) has greater efficacy and broader, more effective dose ranges than AFPep against $E_2$-stimulated immature mouse uterine growth and $ER^+$ human breast cancer cell growth. Furthermore, cyclo [EKTOVNOGN] (SEQ ID NO: 13) FI has significantly greater efficacy than AFPep at higher doses. At higher doses AFPep loses activity whereas cyclo[EKTOVNOGN] (SEQ ID NO: 13) FI maintained biological activity. The superiority of the dose-response profile cyclo[EKTOVNOGN] (SEQ ID NO: 13) FI over the dose response profile of AFPep increases its attractiveness as the lead peptide. It is important to note that cyclo[EKTOVNOGN] (SEQ ID NO: 13) FI showed significant inhibition of MCF-7 $ER^+$ human breast cancer xenografts by many routes of administration (subcutaneous, intraperitoneal, or oral gavage). This suggests that cyclo[EKTOVNOGN] (SEQ ID NO: 13) FI is a potential therapeutic agent for the breast cancer.

In the design of 'ring and tail' peptides, hydrophobicity or hydrophilicity of the 'tail' was a critical part of the design. Aromaticity/hydrophobicity of the 'tail' may play a role in enhancing the dose profile of AFPep. This project showed (FIGS. 31 and 32) that hydrophobicity in the 'tail' region of the peptide is important to maintain biological activity at high doses. Hydrophilicity of the 'tail' had a significantly negative impact on the biological activity of the peptide. Hydrophilic analogs show significantly lower activity than AFPep with little or no biological activity against $E_2$-stimulated growth. In contrast, the hydrophobic analogs had equal or significantly better efficacy in the inhibition of $E_2$-stimulated growth compared to AFPep. These observations suggest that the nature of the 'tail' has a significant influence on the biological activity of the 'ring and tail' analogs, perhaps through its fit with the receptor.

In specific aim 2, it was hypothesized that 'ring and tail' analogs will have greater efficacy and broader, more effective dose response than AFPep. It has been shown that cyclo [EKTOVNOGN] (SEQ ID NO: 13) FI exhibits these properties in the inhibition of $E_2$-stimulated mouse uterine growth and T47D cell proliferation. Therefore, the hypothesis cannot be rejected.

In summary, we have used a novel strategy to synthesize 'ring and tail' peptides containing amino acid tails of different characteristics. We have shown that the 9-peptide ring and tail analog has greater efficacy and a broader, more effective dose range than AFPep. Although the MW of AFPep has increased, the peptidic concepts have been maintained by incorporating only amino acids into the peptide chain. In so doing, we maintained the integrity of cyclo[EKTOVNOGN] (SEQ ID NO: 13) FI as a non-toxic drug candidate and created an analog that is superior to AFPep in terms of efficacy and dose response profile. Therefore, cyclo[EKTOVNOGN] (SEQ ID NO: 13) FI is a very promising candidate as an anticancer drug. Furthermore, this synthesis strategy can be used as a tool to synthesize a library of 'ring and tail' analogs that may be used in biological experiments to elucidate the molecular mechanism of AFP-derived peptides.

'Ring and tail' analogs were then used to elucidate the mechanism of action of AFPep. As discussed above, a hydrophobic 'tail' on AFPep enhances efficacy and broadens the effective dose range whereas a hydrophilic 'tail' decreases the efficacy and dose range of AFPep. Based on the observation that AFPep has a biphasic dose-response curve, a model (FIG. 34) was developed to explain what might be happening pharmacologically between AFP-derived peptides and the target molecules. We postulate that there are two receptors to which AFPep binds: a high affinity receptor and a low affinity receptor. At low dose AFPep binds to the high affinity receptor and exhibits an upward swing in its dose-response curve. At high dose, AFPep binds to the low affinity receptor and exhibits a downward swing in its dose-response curve. The 'ring and tail' peptide that has a hydrophobic 'tail' binds to the high affinity receptor and exhibits a broader, more effective dose range. The 'ring and tail' peptide with a hydrophilic 'tail' binds to the low affinity and a small amount may bind to the high affinity receptor to exhibit this shape of the curve.

To test this model, a 'ring and tail' peptide was designed by making a simple amino acid substitution in the pharmacophore of the 'ring and tail' hydrophilic peptide. When this analog binds to the low affinity receptor there is little or no response. This analog was evaluated in the uterine growth inhibition assay. In the presence of this analog, AFPep binds only to the high affinity receptor and exhibits a sigmoidal dose range curve.

Cellular and Molecular Mechanism Studies

A concerted effort has been made by our laboratory and others to elucidate the mechanism of action of AFPep. However, there is limited knowledge of the receptor(s) and mode of action of the antiestrogenic effect. What is known is that AFPep does not bind to the $E_2$-binding site of the estrogen receptor (21), indicating its antiestrogenic mode of action is completely different from that of tamoxifen. AFPep significantly inhibited the $E_2$-induced estrogen receptor phosphorylation at serine-118 (22), and significantly increased serine-15 phosphorylation on p53 (23). AFPep increases nuclear p21Cip1 activation (202), which may suggest that it is acting through p21Cip1 to inhibit the proliferation of ER+ human breast cancer cells. Subsequently, AFPep has been shown to prevent the transactivation of c-erb2 leading dephosphorylated ERK1/2 after stimulation by $E_2$ or EGF in MCF-7 cells (285). It has been shown that phosphorylated ERK is involved in the regulation of cell proliferation (294) and it has been postulated that p21Cip1 and cyclin regulation of the cell cycle may be controlled by ERK (295). Therefore, it would be useful to investigate the link between Ras/ERK pathway and cell cycle regulators such as the cyclins, p21Cip1, and p53 to determine the cellular and molecular mechanism of AFP-derived peptides in the inhibition of $E_2$-stimulated growth of breast cancer cells.

Pharmacokinetic and Pharmacodynamic Studies

In order to introduce the lead peptide to clinical trials, information about its pharmacokinetics and pharmacodynamics is required. Pharmacokinetics is the study of the effect of the body on drug level over time. It has been shown that our lead peptide candidates are active after oral administration. This brings to prominence the need for bioavailability, distribution, metabolism, and excretion studies to ascertain what quantities of peptide would need to be given by oral route. To study this, radiolabeled peptide could be given to whole animals at various doses by oral gavage, or by intravenous injection via tail vein. Aliquots of blood will be collected, at multiple time points thereafter. The blood concentration data will be plotted against time to generate the maximum plasma concentration, the maximum time to reach maximum concentration, and the half-life of the peptide from the pharmacokinetic profile. The area under the concentration-time curve will be calculated using the linear trapezoidal rule from kinetic data that will be collected from individual values. The relative oral bioavailability will be calculated from the dose-corrected area under the curve from the oral versus intravenous administrations. The extent to which the peptide remains intact will be assessed by use of a simple reverse phase purification step that cleanly separates intact lead peptide from metabolites. It will also be important to administer the labeled peptide to tumor bearing animals and assess the extent to which the peptide is found within the tumors. At various times after bolus iv administration of lead peptide, animals will be sacrificed and subject to necropsy; major organs, tumors, and blood will be collected and measured for radiolabeled peptide.

Pharmacodynamics is the effect the drug has on the body. Information about the efficacy, potency, and affinity of the lead peptide will be needed before it is brought to clinical trials. The laboratory has demonstrated efficacy in therapeutic use for AFPep, TOVNOGNEK (SEQ ID NO: 28), and cyclo [EKTOVNOGN] (SEQ ID NO: 13) FI. Efficacy for AFPep in cancer prevention has also been documented. Prevention studies have not been done with TOVNOGNEK (SEQ ID NO: 28) and cyclo[EKTOVNOGN] (SEQ ID NO: 13) FI. When in vivo therapeutic and prevention studies are performed using these analogs, dose/concentration-response curves should be developed and IC50s calculated for the analogs of AFPep to determine how the potency of these analogs compares to that of AFPep. At present, the receptor(s) for AFPep-derived peptides is unknown. Thus it would be difficult to perform binding studies to determine the affinity of these peptides for the receptor(s). What has been established is that these peptides work on ER+ cells. Therefore, it would be interesting to see if these analogs accumulate in ER+ cells and not in ER− cells and to measure cellular uptake and retention of these peptides. Competition studies could be performed using analogs of AFPep that are known to be biologically inactive.

In this research project two approaches were employed to develop analogs of AFPep that are highly effective in the inhibition of $E_2$-stimulated growth. The first approach developed small analogs of AFPep. The concept was that smaller analogs would be more drug-like than AFPep and therefore they would have higher efficacies. A number of these analogs inhibited $E_2$-stimulated growth in vivo and in vitro. Our results showed smaller analogs did not have higher efficacy than AFPep, even though they conformed better than AFPep to Lipinski's RO5. There was a 5-mer peptide (TOVNO) that had similar efficacy to AFPep, but its dose response profiles in the inhibition of $E_2$-stimulated mouse uterine growth and T47D human ER+ breast cancer cell growth were undesirable. This analog is drug-like and could be a good anticancer agent. However, the goal was to develop analogs that are superior to AFPep and TOVNO (SEQ ID NO: 7) is not.

A linear 9-mer peptide TOVNOGNEK (SEQ ID NO: 28) was developed and interestingly it has efficacy equivalent to AFPep in the inhibition of MCF-7 ER+ human breast cancer xenografts in mice, and a superior dose response profile as an antiestrogenic and anticancer agent. It is postulated that this analog is a metabolite of AFPep. TOVNOGNEK (SEQ ID NO: 28) contains the same types and number of amino acids as AFPep. It is MW=986 g/mol whereas the MW of AFPep is 970 g/mol, so it is not smaller than AFPep. TOVNOGNEK (SEQ ID NO: 28) does not conform to Lipinski's RO5, but it does effectively inhibit $E_2$-stimulated growth. In addition, it is linear and therefore easier to synthesize than AFPep.

The second approach was to develop 'ring and tail' analogs that would be highly effective and have enhanced dose response profiles as antiestrogenic and anticancer agent. This strategy used rational drug design to synthesize AFPep bearing hydrophobic or hydrophilic amino acid 'tails'. These analogs had higher MW than AFPep, which is divergent from work done in section III. However, the high MW of the 'ring and tail' analogs did not affect the hydrophobic-tail analogs effectiveness as antiestrogenic and anticancer agents. The result suggests that hydrophobicity in the 'tail' region enhances efficacy as well as dose response profile. It has been shown that the optimal 'ring and tail' (cyclo[EKTOVNGN] (SEQ ID NO: 13) FI) is superior to AFPep.

An interesting concept in the development of analogs of AFPep, for increased efficacy and enhanced dose response, was that analogs smaller than 9 amino acids should be more drug-like than AFPep. We showed that linear analogs as small as 5 amino acids had similar efficacies to AFPep. However, the cyclic analogs of the same number and types of amino acids as those linear analogs had significantly lower efficacies than AFPep. We postulate that the optimal ring size for maximal inhibitory activity is 9 amino acids. The cyclization of smaller analogs distorts the active conformation leading to decreased biological activity.

Peptidomimetics

In addition to the peptide compounds described herein, the invention also contemplates that other sterically similar compounds may be formulated to mimic the key portions of the peptide structure and that such compounds may also be used in the same manner as the peptides of the invention. This may be achieved by techniques of molecular modeling and chemical design known to those of skill in the art. In one embodiment, for example, the peptides of the invention are modified to produce peptide mimetics by replacement of one or more naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclics. For example, proline analogs can be made in which the ring size of the proline residue is changed from 5 members to 4, 6, or 7 members. Cyclic groups can be saturated or unsaturated, and if unsaturated, can be aromatic or non-aromatic. Heterocyclic groups can contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl. Peptidomimetics may also have amino acid residues that have been chemically modified by phosphorylation, sulfonation, biotinylation, or the addition or removal of other moieties.

A variety of techniques are available for constructing peptide mimetics with the same or similar desired biological activity as the corresponding native but with more favorable activity than the peptide with respect to solubility, stability, and/or susceptibility to hydrolysis or proteolysis (see, e.g., Morgan & Gainor, *Ann. Rep. Med. Chem.* 24, 243-252, 1989). Certain peptidomimetic compounds are based upon the amino acid sequence of the peptides of the invention. Often, peptidomimetic compounds are synthetic compounds having a three-dimensional structure (i.e. a "peptide motif") based upon the three-dimensional structure of a selected peptide. The peptide motif provides the peptidomimetic compound with the desired biological activity, i.e., binding to IAP, wherein the binding activity of the mimetic compound is not substantially reduced, and is often the same as or greater than the activity of the native peptide on which the mimetic is modeled. Peptidomimetic compounds can have additional characteristics that enhance their therapeutic application, such as increased cell permeability, greater affinity and/or avidity and prolonged biological half-life.

Peptidomimetic design strategies are readily available in the art (see, e.g., Ripka & Rich, *Curr. Op. Chem. Biol.* 2, 441-452, 1998; Hruby et al., *Curr. Op. Chem. Biol.* 1, 114-119, 1997; Hruby & Balse, *Curr. Med. Chem.* 9, 945-970, 2000). One class of peptidomimetics comprises a backbone that is partially or completely non-peptide, but mimics the peptide backbone atom for atom and comprises side groups that likewise mimic the functionality of the side groups of the native amino acid residues. Several types of chemical bonds, e.g. ester, thioester, thioamide, retroamide, reduced carbonyl, dimethylene and ketomethylene bonds, are known in the art to be generally useful substitutes for peptide bonds in the construction of protease-resistant peptidomimetics. Another class of peptidomimetics comprises a small non-peptide molecule that binds to another peptide or protein, but which is not necessarily a structural mimetic of the native peptide. Yet another class of peptidomimetics has arisen from combinatorial chemistry and the generation of massive chemical libraries. These generally comprise novel templates which, though structurally unrelated to the native peptide, possess necessary functional groups positioned on a nonpeptide scaffold to serve as "topographical" mimetics of the original peptide (Ripka & Rich, 1998, supra).

Pharmaceutical Compositions

The peptides of the invention are useful in a method of reducing estrogen-stimulated growth of cells by contacting the cells with the peptide. Accordingly, the compounds of the invention can be administered alone or as a pharmaceutical composition, systemically, regionally (e.g., directed towards an organ or tissue), or locally (e.g., directly into a tumor mass), in accordance with any protocol or route that achieves the desired effect. The compounds and pharmaceutical compositions can be administered as a single or multiple dose each day (e.g., at a low dose), or intermittently (e.g., every other day, once a week, etc. at a higher dose). The compounds and pharmaceutical compositions can be administered via inhalation (e.g., intra-tracheal), orally, intravenously, intraarterially, intravascularly, intrathecally, intraperitonealy, intramuscularly, subcutaneously, intracavity, transdermally (e.g., topical), transmucosally (e.g., buccal, bladder, vaginal, uterine, rectal, or nasal), by multiple administrations, sustained release (e.g., gradual perfusion over time) or a single bolus. Implantable devices, including microfabricated devices, for administering drugs are well known and are also applicable for delivering compounds of the invention to a subject.

As used herein the term "pharmaceutically acceptable" and "physiologically acceptable" includes solvents (aqueous or non-aqueous), solutions, emulsions, dispersion media, coatings, isotonic and absorption promoting or delaying agents, compatible with pharmaceutical administration. A "pharmaceutical composition" or "pharmaceutical formulation" therefore refers to a composition suitable for pharmaceutical use in a subject. The pharmaceutical compositions and formulations include a therapeutically effective amount of the compound of the invention, for example, an effective amount of a peptide or peptidomimetic, and a pharmaceutically or physiologically acceptable carrier.

As will be known to the skilled artisan, pharmaceutical compositions can be formulated to be compatible with a particular route of administration, systemic or local. Thus, pharmaceutical compositions include carriers, diluents, or excipients suitable for administration by various routes.

Formulations for enteral (oral) administration can be contained in a tablet (coated or uncoated), capsule (hard or soft), microsphere, emulsion, powder, granule, crystal, suspension, syrup or elixir. Conventional nontoxic solid carriers which include, for example, pharmaceutical grades of mannitol, lactose, starch, magnesium stearate, sodium saccharin, talcum, cellulose, glucose, sucrose, magnesium carbonate, can be used to prepare solid formulations. Supplementary active compounds (e.g., preservatives, antibacterial, antiviral and antifungal agents) can also be incorporated into the formulations. A liquid formulation can also be used for enteral administration. The carrier can be selected from various oils including petroleum, animal, vegetable or synthetic, for example, peanut oil, soybean oil, mineral oil, sesame oil. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Pharmaceutical compositions for enteral, parenteral, or transmucosal delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65-75; Warren (1997) J. Neurol. Sci. 152:31-38; and Tonegawa (1997) J. Exp. Med. 186:507-515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, sodium chloride may be included in the composition. The resulting solutions can be packaged for use as is, or lyophilized, the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760-1764; Samanen (1996) J. Pharm. Pharmacol. 48:119-135; and U.S. Pat. No. 5,391,377, describing lipid compositions for oral delivery of therapeutic agents).

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be through nasal sprays or suppositories (see, e.g., Sayani (1996) "Systemic delivery of peptides and proteins across absorptive mucosae" Crit. Rev. Ther. Drug Carrier Syst. 13:85-184). For transdermal administration, the active compound can be formulated into ointments, salves, gels, or creams as generally known in the art. Transdermal delivery systems can also be achieved using patches.

For inhalation delivery, the pharmaceutical formulation can be administered in the form of an aerosol or mist. For aerosol administration, the formulation can be supplied in finely divided form along with a surfactant and propellant. In another embodiment, the device for delivering the formulation to respiratory tissue is in which the formulation vaporizes. Other delivery systems known in the art include dry powder aerosols, liquid delivery systems, inhalers, air jet nebulizers and propellant systems (see, e.g., Patton (1998) Biotechniques 16:141-143; Dura Pharmaceuticals, San Diego, Calif.; Aradigm, Hayward, Calif.; Aerogen, Santa Clara, Calif.; and Inhale Therapeutic Systems, San Carlos, Calif.).

Biodegradable, biocompatable polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501,728; 4,522,811; 4,837,028; 6,110,490; 6,096,716; 5,283,185; 5,279,833; Akimaru (1995) Cytokines Mol. Ther. 1:197-210; Alving (1995) Immunol. Rev. 145:5-31; and Szoka (1980) Ann. Rev. Biophys. Bioeng. 9:467). Biodegradeable microspheres or capsules or other biodegradable polymer configurations capable of sustained delivery of small molecules including peptides are known in the art (see, e.g., Putney (1998) Nat. Biotechnol. 16:153-157). Compounds of the invention can be incorporated within micelles (see, e.g., Suntres (1994) J. Pharm. Pharmacol. 46:23-28; Woodle (1992) Pharm. Res. 9:260-265). Peptides can be attached to the surface of the lipid monolayer or bilayer. For example, peptides can be attached to hydrazide-PEG-(distearoylphosphatidyl) ethanolamine-containing liposomes (see, e.g., Zalipsky (1995) Bioconjug. Chem. 6:705-708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5-8), transmucosal, or oral administration.

A pharmaceutically acceptable formulation can incorporate about 1% to 99.9% of active ingredient (e.g., peptide or peptidomimetic). The pharmaceutical compositions can be sterilized by conventional, well-known sterilization techniques, or can be sterile filtered.

Additional pharmaceutical formulations and delivery systems are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technomic Publishing Co., Inc., Lancaster, Pa., (1993); and Poznansky et al., *Drug Delivery Systems*, R. L. Juliano, ed., Oxford, N.Y. (1980), pp. 253-315).

The pharmaceutical formulations can be packaged in unit dosage form for ease of administration and uniformity of dosage. "Unit dosage form" as used herein refers to physically discrete unitary dosages for administration to the subject to be treated; each unit contains a predetermined quantity of compound that produces a desired effect in combination with a pharmaceutical carrier or excipient.

The invention further provides kits including invention compounds and pharmaceutical formulations thereof, optionally packaged into suitable packaging material. A kit typically includes a label or packaging insert including a description of the components or instructions for use in vitro, in vivo, or ex vivo, of the components therein. A kit can contain a collection of such components, e.g., two or more invention compounds or an invention compound in combination with a nucleic acid damaging agent or an anti-proliferative agent.

EXAMPLES

Peptide Synthesis

Linear Peptides

Figure 3:
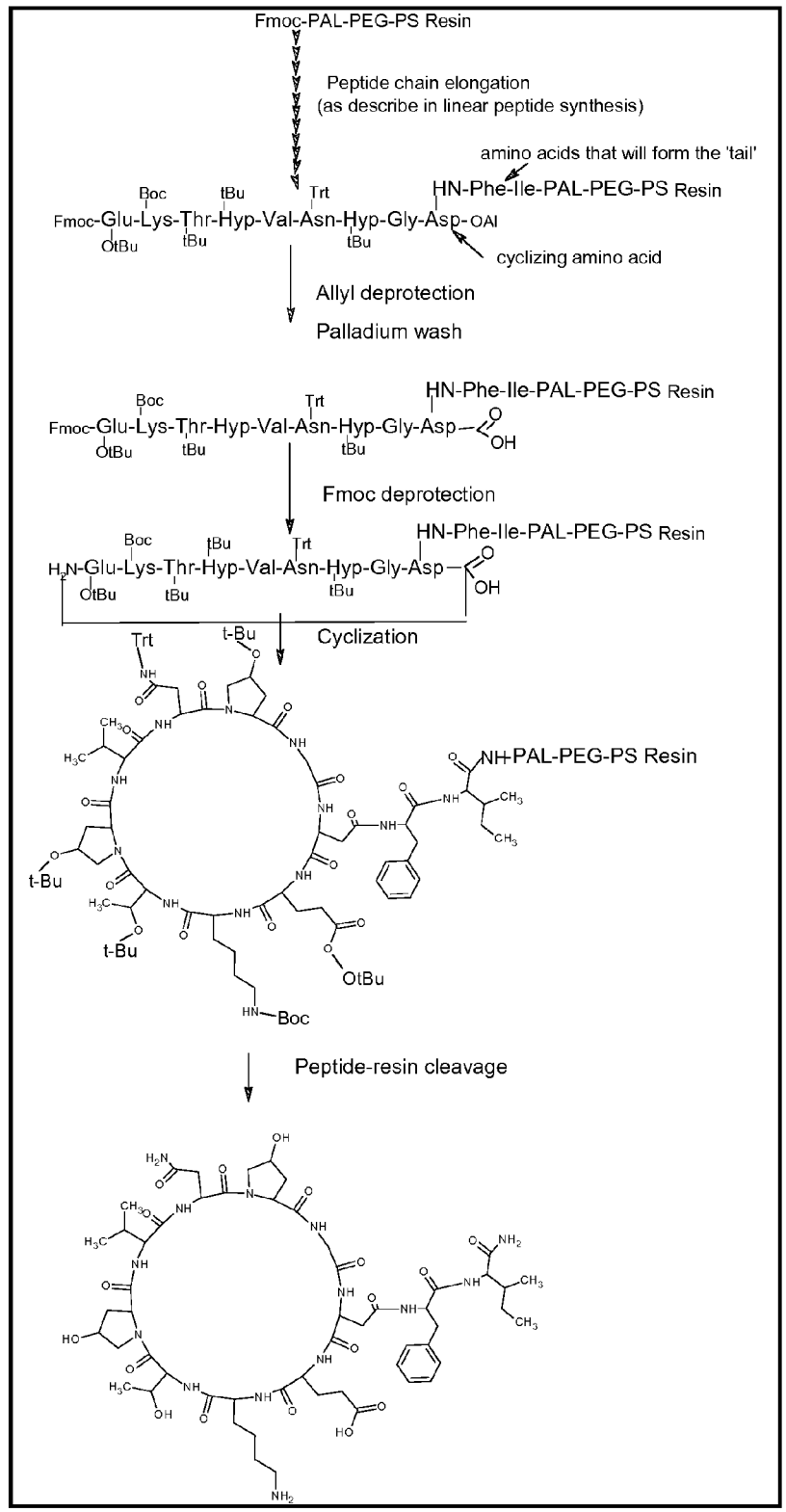
FIG. 3 depicts the scheme for synthesis of a ring and tail cyclic peptide of the invention.

As shown in FIG. 3, peptides were prepared using Fmoc solid-phase synthesis as previously described by Mesfin et al. (25). A Pioneer Peptide Synthesis system (Applied Biosystems, Inc.) or a Thuramed T100 Peptide Synthesis system (Advanced ChemTech) was used to assemble the growing peptide chain on Fmoc-PAL-PEG-PS resin beginning with the C-terminus using $N^\alpha$-protected amino acids. Activation of the C-terminus of incoming amino acids was accomplished by treatment with HATU and DIPEA. Following synthesis, linear peptides were cleaved from the resin by incubation for approximately 2 h in 9.5 mL of TFA:anisole:EDT (90:2.5:2.5) per 0.1 mmol of peptide (0.5 g resin) and side-chain protective groups were removed concurrently. Peptides were precipitated by addition of cold (−20° C.) diethyl ether and washed by repeated extraction with diethyl ether and then with ethylacetate/diethyl ether (1.5:1). The peptide was dissolved in a volume of deionized water to achieve a concentration of 5-10 mg/mL and lyophilized for 48 hours.

Cyclization of peptides was accomplished using methods described by Kates et al. (278) and Mesfin et at (26). Briefly, $N^\alpha$-Fmoc-L-aspartic acid-alpha-allyl ester at the C-terminus of the synthetic peptide was coupled to the resin via the gamma carboxylic acid. Removal of the $N^\alpha$-Fmoc allowed the remaining amino acids to be incorporated sequentially into the growing peptide. A free alpha-carboxyl group was then generated upon removal of the allyl group from the C-terminal Asp (26, 278, 279). The peptidyl-resin was dried and flushed with nitrogen delivered through a septum. A catalyst solution was prepared separately by mixing 3 equivalent of Pd $(PPh_3)_4$ in $CHCl_3$/acetic acid/N-4-methylmorpholine (15 mL/g of resin) and dissolved by bubbling nitrogen through the solution. The catalyst was transferred to the tube containing peptidyl-resin using a gas-tight syringe, and mixed for 2 h. Peptidyl-resin was washed consecutively with 0.5% DIPEA in DMF and 0.5% w/w DEDC in DMF to remove the catalyst. Fmoc was removed from the N-terminus and the free alpha-carboxyl group was then coupled to the free N-terminal residue of the peptide (while on the resin) in order to generate the cyclic peptide, which was then removed from the resin in such a way as to yield the gamma-carboxamido derivative (i.e., Asn).

'Ring and Tail' Peptide Synthesis

One scheme for the production of the cyclic "ring and tail" peptides of the invention is shown in FIG. 3. Peptides were assembled on PAL-PEG-PS resin beginning with the C-terminus using amino acids that formed the 'tail'. At the N-terminal end of the 'tail', Fmoc-Asp (OAll) was coupled through its γ-carboxylic acid, leaving the α-carboxylic group protected (with the allyl group) for later cyclization reaction. The peptide ring was assembled using $N^\alpha$-Fmoc protected amino acids, through sequential coupling of the remaining residues. Cyclization was achieved as described above. First, the allyl group from α-carbonyl of Asp was removed (278, 279). Secondly, Fmoc deprotection of the $N^\alpha$ terminus of the final amino acid provided a free amino group. Coupling of the C-terminus of Asp to the deprotected $N^\alpha$ terminus formed the ring in the presence of PyBOP/HOBt/DIPEA. The cyclic peptide was cleaved from the resin, which allowed the 'tail'-forming amino acid(s) to hang outside the peptide ring.

Purification of Peptides

Peptides were purified using a reverse-phase $C_{18}$ Sep-Pak cartridge (Waters, Milford, Mass., USA) as previously described by DeFreest et al. Briefly, a sample containing a peptide of unknown purity was loaded onto a pre-washed cartridge and the sample was sequentially eluted with water, 10%, 30%, and 60% acetonitrile in water. The fraction containing peptide was then lyophilized. Peptides used for structure-activity relationship analysis were purified prior to use in biological assays, and those used in biological assays were at 95% or greater purity. Peptides were evaluated by mass spectrometry.

Mass Spectrometry

Matrix assisted laser desorption ionization mass spectra (MALDI-MS) were recorded on a Voyager-DE PRO BioSpectrometry Workstation from Applied Biosystems. Samples were dissolved in 50% aqueous acetonitrile and α-cyano-4-hydroxycinnamic acid was used as matrix. Positive ion electrospray ionization mass spectra (ESI-MS) were recorded on a micromass Q-ToF-2 mass spectrometer. Samples were dissolved in 70% aqueous methanol and infused into the electrospray chamber with a needle voltage of 0.9 kV at a flow rate of 40 nl/min.

Peptides were synthesized using Fmoc solid-phase peptide synthesis on a Pioneer Peptide Synthesis System (PerSeptive Biosystems, Inc., Framingham, Mass.). Briefly, peptides were assembled on Fmoc-PAL-PEG-PS-resin (Applied Biosystems, Inc.) from the C-terminus, reacting the deblocked N-terminus of the incoming amino acid to form an amide bond. Amino acids used in the synthesis had their $N^\alpha$-amino group protected by the 9-fluorenylmethyloxycarbonyl (Fmoc) group, which was removed by piperidine at the end of each cycle in the synthesis. Side-chain protecting groups of amino acids were Asn (Trt), Gln (Trt), Glu (OtBu), Hyp (tBu), Thr (tBu) which were deprotected by trifluoroacetic acid (TFA) after peptide synthesis. The carboxyl group of the amino acid was activated with O-(7-azabenzotriazol-1-yl)-1,1,2,3-tetramethyluronium hexafluorophosphate (HATU).

After synthesis was completed, the resin was washed three times with 100% propanol and the cleavage reaction was achieved by incubating the resin in 10 ml TFA/thioanisole/anisole/1,2-ethanedithiol (90:5:2:3) per 0.5 g resin for 5 hours. The cleavage reaction mixture was filtered using a sintered glass funnel to separate the solid resin from the peptide solution. Filtrate volume was reduced to 1 ml by evaporation facilitated with a gentle stream of air and the peptides were precipitated by addition of 15 ml dry-ice-chilled ethyl ether. The peptides were allowed to settle for 5 min at $-80°$ C., and the supernatant was aspirated. The peptides were then washed twice in similar manner with 15 ml of ethyl acetate/diethylether (1.5:1, room temperature), the peptides were dissolved in deionized water, purified by reverse-phase HPLC, lyophilized and stored at $-20°$ C.

The anti-estrogenic activity of each peptide was then determined using the immature mouse uterine growth assay, MCF-7 xenograft assay, and cancer prevention assay, all as previously described.

Immature Mouse Uterine Growth Assay

The anti-breast cancer activity of the linear and cyclic 8-mer and 9-mer AFP-derived peptides is well-documented using the immature mouse uterine growth assay and the human breast cancer xenograft assay; there is a strong correlation between the results of these two assays. To evaluate peptide-induced inhibition by the peptide of the present invention of estrogen-stimulated proliferation of normal tissue, the immature mouse uterine growth assay was utilized. Briefly, 13-15 day-old Swiss/Webster female mice, 6-8 g in body weight, were distributed into treatment groups of 5 mice per group so that each group contained animals of the same range of body weight. The peptide of the invention was injected i.p., s.c., or p.o. into the mice. One hour later, estradiol ($E_2$) or vehicle control for $E_2$ was injected i.p. Twenty-two hours after the second injection, uteri were harvested, trimmed free of mesenteries, and immediately weighed. The uterine weights were normalized to mouse body weights to compensate for differences in body weight among litters of the same age. Experiments employed a minimum of five mice per group and the mean normalized uterine weight±SE for each group was calculated. Percent growth inhibition in a test group was calculated from normalized uterine wet weights as described below.

$$\text{Growth inhibition (\%)} = \frac{\text{Full } E_2 \text{ stimulation} - E_2 \text{ stimulation in test group}}{\text{Full } E_2 \text{ stimulation} - \text{no } E_2 \text{ stimulation}} \times 100\%$$

Xenograft Assay

The peptides of the invention were evaluated for their ability to inhibit tumor growth in a human tumor xenograft assay. Briefly, MCF-7 human breast cancer cells were obtained from ATCC® (Rockville, Md.) and were grown in DMEM supplemented with 5% FCS, 1% non-essential amino acids, 10 ng/ml insulin, 2 mM L-glutamine, 100 units/ml penicillin, and 100 µg/ml streptomycin. MCF-7 cells from culture were solidified into a fibrin clot. The tumor-containing clots were cut into pieces about 1.5 mm in diameter and implanted under the kidney capsule of severe combined immunodeficient (ICR-SCID) mice (Taconic Farms, Germantown, N.Y.) as described in Bennett et al. (Clin. Cancer Res. 1998; 4:2877-84).

Estrogen supplementation of mice was required for the growth of MCF-7 tumors. Supplementation was accomplished by s.c. implantation of a Silastic tubing capsule containing solid $E_2$ (2 mm in length) inserted on the day of tumor implantation. Tumor size was evaluated during survival laparotomy using a dissecting microscope at the time of tumor implantation and at days 15 and 30 after tumor implantation. Results are represented as the change in mean tumor volume ($mm^3$).

Prevention Assay

The prevention study uses the methodology of Grubbs et al. (J. Natl. Cancer Inst. 71:625-628, 1983; Anticancer Res. 6:1395-1400, 1986) to test the ability of AFP peptides to prevent N-methyl-N-nitrosourea (MNU)-induced breast cancers in rats. Briefly, female rats were housed three per cage in a room maintained at 72±2° F. and artificially lighted for 12 hours daily. At 50 days of age, rats received a single injection of MNU (50 mg/kg body weight) or vehicle in the jugular vein. NMU was given to animals from the various treatment groups according to a predetermined randomization chart to ensure uniform distribution of the carcinogen across the groups. Beginning 10 days after MNU exposure, treatment with AFP peptide by s.c. injection occurred once daily for 23 days, a time chosen to mimic the gestation period of rats, or for loner or shorter times. The peptide was diluted in saline and was given in an investigator-blinded manner at doses between 0.03 and 0.27 mg/rat daily in a volume of 0.2 ml. The control group of animals received daily 0.2 ml s.c. injections of saline for the same time as AFP peptide administration. Animals in the positive control group received only MNU treatment and experienced the maximal number of tumors. The negative control group of rats received no MNU and no AFP peptide. These animals generated no spontaneous tumors throughout the course of the study. Additional groups of animals received MNU Beginning 30 days after MNU treatment, all rats were palpated twice weekly for detection of mammary tumors, noting number, location, and size. Tumor burden was determined noninvasively with calipers by measuring the long (D) and short (d) diameters. Assuming that tumors were ellipsoid shaped, tumor volume was estimated as $(\pi/6)(d)^2 (D)$. All animals were checked daily for signs of toxicity. Most studies were terminated 100 days following MNU administration and at necropsy, tumors were dissected weighed.

The ability to inhibit $E_2$-stimulated growth of normal mouse uterus was used as a screening assay for biological activity of AFPep analogs. In general, inhibitory activity ≥20% is considered to be biologically significant. Each analog's inhibitory effect on E$_2$-stimulated growth was compared to AFPep (a positive control) and to PGVGQ (SEQ ID NO: 29; a negative control). PGVGQ (SEQ ID NO: 29; amino acids 478-482 of AFP) is a portion of the primary structure of AFP near to the anti-cancer active site of AFP and is comprised of amino acids (P, V, and G) that are important components of AFPep. A scrambled analog of AFPep was not used because some scrambled peptides retain low biological activity (data not shown).

Ring and Tail Antagonist

Figure 10:
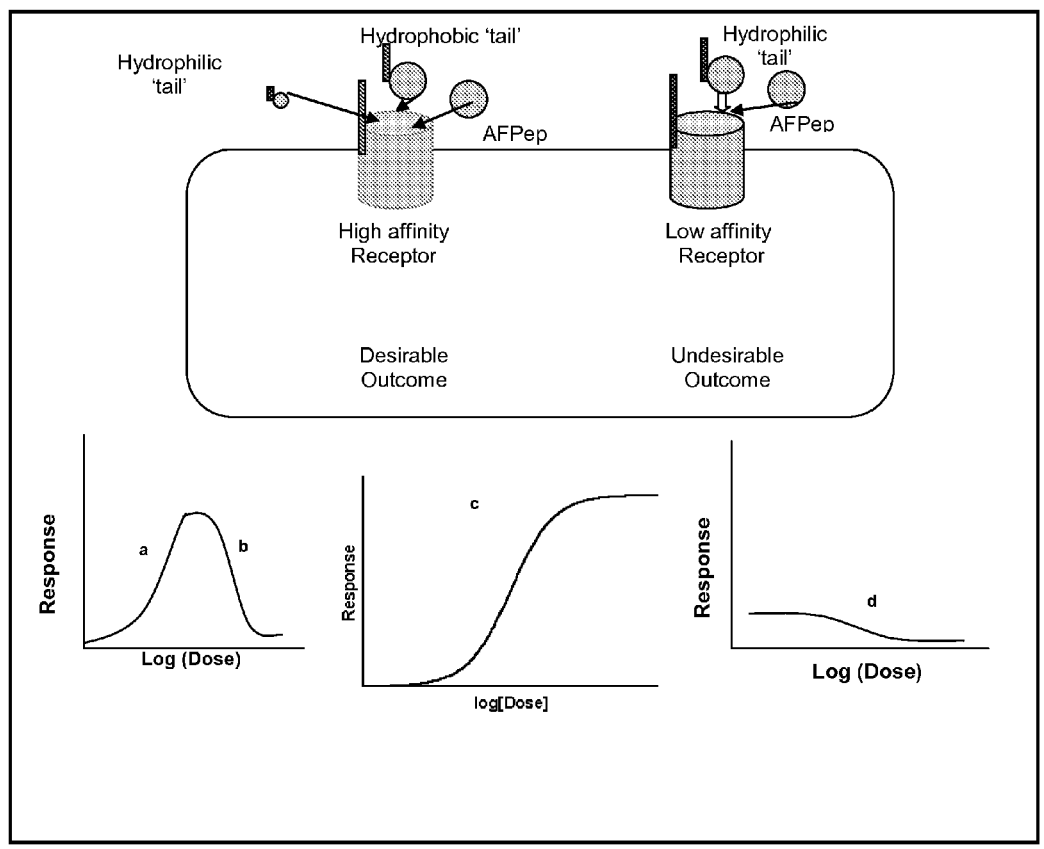
FIG. 10 shows a model of a putative two-receptor model of AFP anti-estrogenic action and its relationship to dose response.

AFPep is a 9-amino acid peptide derived from alpha-fetoprotein, a protein of pregnancy. Based on prior data which show that AFPep exhibits a biphasic dose-response curve, we theorized that AFPep binds to a two-receptor system. (Receptors to which AFPep binds are believed to be receptors for AFP.) One binding site is a high affinity receptor that leads to inhibition of cancer growth. A second binding site is a lower affinity receptor that leads to promotion of cancer growth (See FIG. 10).

At low dose, AFPep binds to the high affinity receptor and exhibits the upward swing of the dose response curve (FIG. 10a). At high dose, AFPep binds to the low affinity receptor and exhibits the downward swing of the curve (b). The 'ring and tail' peptide that has a hydrophobic 'tail' binds to the high affinity receptor and exhibits a broader, more effective dose range (c). The 'ring and tail' peptide with a hydrophilic tail binds to the low affinity receptor and a small amount may bind to the high affinity receptor to exhibit this shape of the curve (d).

In this model, the high affinity receptor leads to inhibition of cancer growth. The lower affinity receptor leads to promotion of cancer growth. It is AFPep's ability to bind to both receptors that induces its undesired biphasic biological behavior. In a dose-response curve of biological activity AFPep's inhibition increases steadily until higher doses are introduced that lead to a decrease in tumor inhibition response.

These observations led to the idea that additional drug design considerations could offer opportunities to render the low affinity receptor completely inactive. In order to achieve this, an analog with a hydrophilic tail (to target the second receptor) was incorporated with an altered pharmacophore (so as to prevent signaling by the receptor). This ring and tail peptide can bind preferentially to the low affinity receptor and shut it down. This analog would be expected to prevent any residual binding to the low affinity receptor of an analog that targets the high affinity receptor.

In order to fully understand the biphasic biological behaviors of AFPep we made various analogs with modifications that would give them a higher attraction to one of the receptors. We utilized an empirical approach of adding hydrophobic or hydrophilic 'tails' to the cyclic peptide in an effort to direct the analog to one receptor or the other. It was understood that hydrophobic tails steer the analogs towards the high affinity receptor and allow for optimal tumor inhibition. Yet these high affinity receptor analogs still exhibited biphasic behavior. Without wishing to be bound by theory, we believe that once all of the high affinity receptors become occupied the remaining analogs will bind to the low affinity receptors.

We have also shown that an analog with a hydrophobic tail binds more strongly towards the low affinity receptor. One approach to deter the biphasic response of AFPep would be an analog that is steered towards the low affinity receptor with a hydrophilic tail and has a modified pharmacophore to enable it to bind and deactivate the receptor. This would elicit a sigmoidal dose response when high doses of the high affinity analog are used.

In one embodiment, an analog which can bind and deactivate the receptor has one modification in the pharmacophore and a lysine hydrophilic tail. By substituting a glycine for the first asparagine in the AFPep hydrophilic analog having the sequence [EKTOVNOGN] (SEQ ID NO: 13) K, an antagonist having the sequence [EKTOVGOGN] (SEQ ID NO: 30) K was created. The change from asparagine to glycine alters the charge of the pharmacophore and also decreases the length of the side group at that point.

Figure 11:
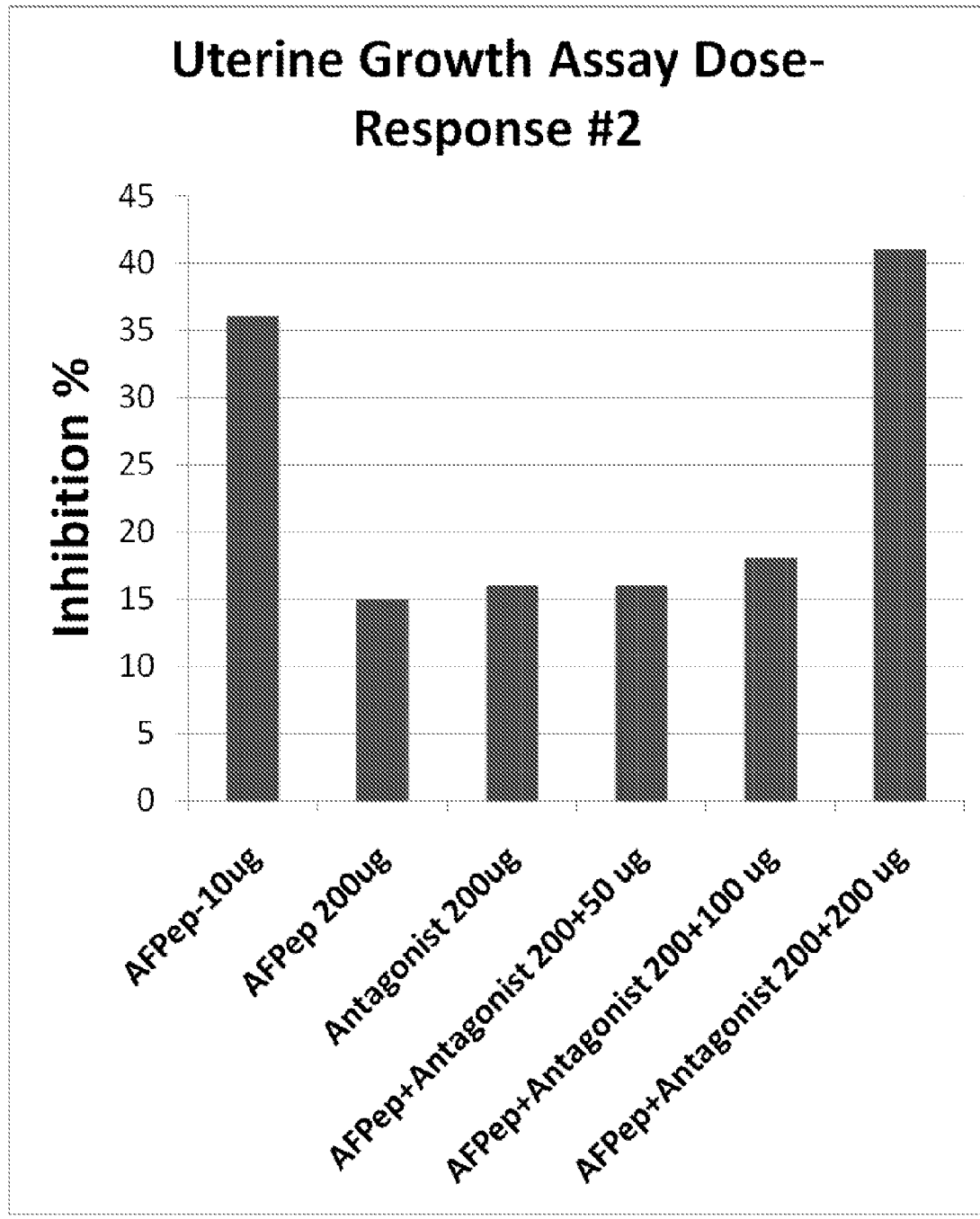
FIG. 11 shows the effect on uterine growth of a combination of AFP and ring and tail antagonist of the invention.

As can be seen in FIG. 11, the level of inhibition that can be achieved with low levels of AFPep, but not higher dosages, is restored by addition of the antagonist analog of the invention.

Figure 12:
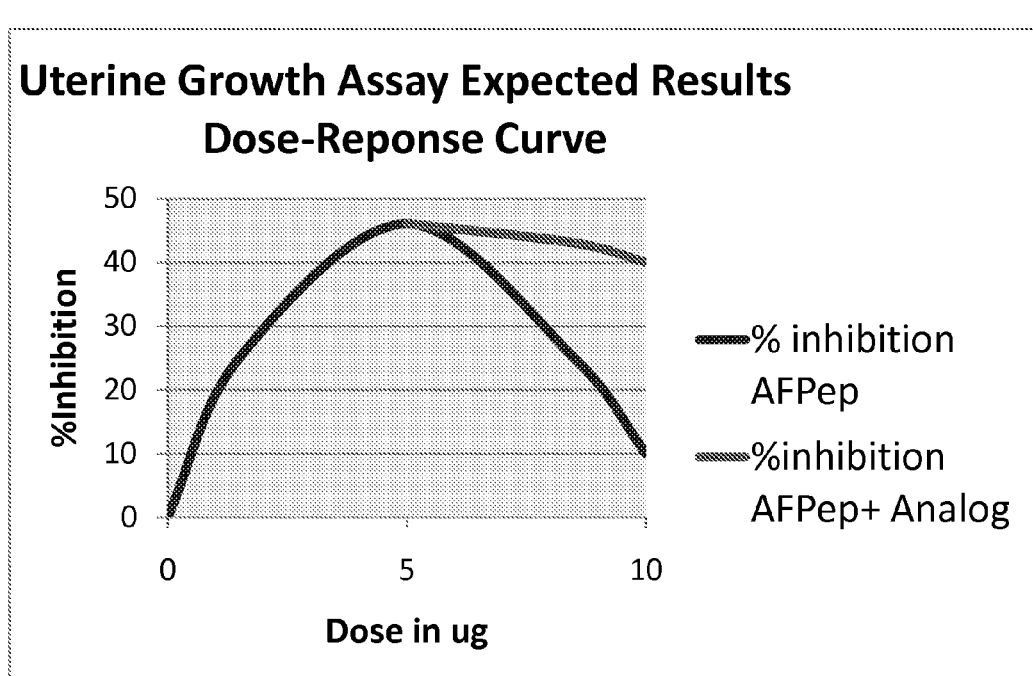
FIG. 12 shows the effect of combining AFPep with an antagonistic AFP analog, i.e., one that has a disrupted pharmacophore and a hydrophilic tail.

Referring to FIG. 12, the biphasic dose response curve seen with AFPep alone can be overcome by using a combination of AFPep and an analog with a hydrophilic tail.

LITERATURE CITED

1. G. I. Abelev, *Advances in Cancer Research* 14, 295 (1971).
2. H. I. Jacobson, J. A. Bennett, G. J. Mizejewski, *Cancer Research* 50, 415 (Jan. 15, 1990).
3. J. A. Bennett, S. J. Zhu, A. Pagano-Mirarchi, T. A. Kellom, H. I. Jacobson, *Clinical Cancer Research* 4, 2877 (November, 1998).
4. F. B. Mesfin, T. T. Andersen, H. I. Jacobson, S. Zhu, J. A. Bennett, *Journal of Peptide Research* 58, 246 (September, 2001).
5. L. A. DeFreest et al., *Journal of Peptide Research* 63, 409 (May, 2004).
6. F. B. Mesfin, J. A. Bennett, H. I. Jacobson, S. J. Zhu, T. T. Andersen, *Biochimica Et Biophysica Acta-Molecular Basis of Disease* 1501, 33 (Apr. 15, 2000).
7. J. A. Bennett, F. B. Mesfin, T. T. Andersen, J. F. Gierthy, H. I. Jacobson, *Proc Natl Acad Science* 99, 2211 (February 2002).
8. L. E. Eisele, F. B. Mesfin, J. A. Bennett, T. T. Andersen, H. I. Jacobson, D. D. Vakharia, R. MacColl, G. J. Mizejewski, *Journal of Peptide Research* 57, 539 (June 2001).
9. L. E. Eisele, F. B. Mesfin, J. A. Bennett, T. T. Andersen, H. I. Jacobson, H. Soldwedel, R. MacColl, G. J. Mizejewski, *Journal of Peptide Research* 57, 29 (January 2001).
10. S. Aggarwal, P. Singh, O. Topaloglu, J. T. Isaacs, S. R. Denmeade, *Cancer Research* 66, 9171 (Sep. 15, 2006).
11. S. Aggarwal, J. L. Harden, S. R. Denmeade, *Bioconjugate Chem.*, 17, 335 (Feb. 8, 2006).
12. P. D. O'Leary, R. A. Hughes, *The Journal of Biological Chemistry*, 278, 25738 (Jul. 11, 2003).

What is claimed is:

1. A cyclic peptide comprising a ring portion and a hydrophobic tail portion, said ring portion comprising from 5-9 amino acids, wherein said ring portion of said peptide comprises an amino acid sequence selected from the group consisting of:

$$AA_1\text{-}AA_2\text{-}AA_3\text{-}AA_4 \quad \text{a)}$$

wherein $AA_1$ is threonine, serine, valine or alanine;
$AA_2$ is hydroxyproline or serine;
$AA_3$ is valine, isoleucine, leucine or threonine; and
$AA_4$ is asparagine or glycine;

$$AA'_1\text{-}AA'_2\text{-}AA'_3\text{-}N\text{-}AA'_4 \quad \text{b)}$$

wherein $AA'_1$ is threonine, serine, valine or alanine;
$AA'_2$ is hydroxyproline or serine;
$AA'_3$ is valine, isoleucine, leucine or threonine; and
$AA'_4$ is hydroxyproline or asparagine; or $$AA''_1\text{-}AA''_2\text{-}N\text{-}AA''_3 \quad \text{c)}$$

wherein $AA''_1$ is hydroxyproline or serine;
$AA''_2$ is valine, isoleucine, leucine or threonine; and
$AA''_3$ hydroxyproline or asparagine; and
said hydrophobic tail portion comprises from 1 to 4 amino acids.

2. The cyclic peptide of claim 1, wherein said tail portion comprises 1-4 amino acids that have hydrophobic side chains.

3. The cyclic peptide of claim 1, wherein said peptide has anti-estrotrophic activity.

4. A cyclic peptide comprising a ring portion and a hydrophobic tail portion, said ring portion comprising from 5-9 amino acids, wherein said ring portion of said peptide comprises an amino acid sequence selected from TPVN (SEQ ID NO: 2), TOVN (SEQ ID NO: 3), TPVNP (SEQ ID NO: 4), TOVNP (SEQ ID NO: 5), TPVNO (SEQ ID NO: 6), TOVNO (SEQ ID NO: 7), PVNPG (SEQ ID NO: 8), OVNOG (SEQ ID NO: 9), KTOVN (SEQ ID NO: 10), KTOVNO (SEQ ID NO: 11), KTOVNOG (SEQ ID NO: 14), KTPVNPG (SEQ ID NO: 15) and EKTOVNOGN (SEQ ID NO: 13).

5. The cyclic peptide of claim 1, wherein the ring portion of said peptide comprises the amino acid sequence EKTOVNOGN (SEQ ID NO. 13).

6. The cyclic peptide of claim 1, wherein said tail portion comprises phenylalanine.

7. The cyclic peptide of claim 6, comprising the amino acid sequence [EKTOVNOGN] (SEQ ID NO: 13) F.

8. The cyclic peptide of claim 1, wherein said tail portion comprises isoleucine.

9. The cyclic peptide of claim 8 comprising the amino acid sequence [EKTOVNOGN]I (SEQ ID NO: 13).

10. The cyclic peptide of claim 1, wherein said tail portion comprises phenylalanine and isoleucine.

11. The cyclic peptide of claim 10 comprising the amino acid sequence [EKTOVNOGN] (SEQ ID NO: 13) FI.

12. A method of reducing estrogen-stimulated growth of cells, the method comprising exposing said cells to the peptide of claim 1.

13. The method of claim 12, comprising exposing the cells to tamoxifen before, during, or after exposing the cells to the peptide.

14. A method for the treatment of breast cancer in a patient comprising administering to the patient a therapeutically effective amount of the peptide of claim 1.

15. A pharmaceutical composition comprising a peptide of claim 1 and a pharmaceutically acceptable carrier.

* * * * *

UNITED STATES PATENT AND TRADEMARK OFFICE
CERTIFICATE OF CORRECTION

PATENT NO. : 9,249,189 B2
APPLICATION NO. : 13/522882
DATED : February 2, 2016
INVENTOR(S) : Thomas T. Andersen et al.

Page 1 of 1

It is certified that error appears in the above-identified patent and that said Letters Patent is hereby corrected as shown below:

In the Specification

Column 1, Line 13, cancel the text beginning with "The present application" to and ending "in this invention." in Column 1, Line 19, and insert the following text:
-- This invention was made with government support under W81XWH-04-1-0486 awarded by the Medical Research and Development Command, R25 GM062460, R15 CA115524, T34 GM008718, and R01 CA102540 awarded by the National Institutes of Health, and CHE0521063, CHE0116435, and CHE0457275 awarded by the National Science Foundation. The government has certain rights in the invention. --

Signed and Sealed this
Sixteenth Day of April, 2024

Katherine Kelly Vidal
*Director of the United States Patent and Trademark Office*